US007082947B2

(12) United States Patent
Smaldone

(10) Patent No.: US 7,082,947 B2
(45) Date of Patent: *Aug. 1, 2006

(54) FACE MASK FOR USE IN PRESSURIZED DRUG DELIVERY SYSTEMS

(76) Inventor: Gerald C. Smaldone, 47 Main St., Setauket, NY (US) 11733-2862

(*) Notice: Subject to any disclaimer, the term of this patent is extended or adjusted under 35 U.S.C. 154(b) by 0 days.

This patent is subject to a terminal disclaimer.

(21) Appl. No.: 10/978,068

(22) Filed: Oct. 28, 2004

(65) Prior Publication Data

US 2005/0150496 A1 Jul. 14, 2005

Related U.S. Application Data

(60) Provisional application No. 60/566,117, filed on Apr. 27, 2004, provisional application No. 60/515,382, filed on Oct. 29, 2003.

(51) Int. Cl.
*A62B 18/08* (2006.01)
*A62B 18/02* (2006.01)

(52) U.S. Cl. .......................... 128/206.23; 128/206.21; 128/206.26; 128/206.28

(58) Field of Classification Search ........... 128/201.15, 128/201.14, 201.17, 203.12, 206.24, 205.25, 128/204.11, 206.23, 200.23, 200.22, 200.21, 128/200.14

See application file for complete search history.

(56) References Cited

U.S. PATENT DOCUMENTS 3,182,659 A * 5/1965 Blount .................. 128/207.12
4,520,509 A * 6/1985 Ward ............................ 2/206
4,641,379 A * 2/1987 Martin ............................. 2/9
4,653,124 A * 3/1987 McNeal et al. ................ 2/427
4,865,027 A * 9/1989 Laanen et al. ......... 128/200.21
5,048,516 A * 9/1991 Soderberg .............. 128/205.25
5,704,063 A * 1/1998 Tilden .............................. 2/9
5,746,201 A * 5/1998 Kidd ..................... 128/206.24
6,085,748 A * 7/2000 Sword et al. .......... 128/206.23
6,340,023 B1 1/2002 Elkins
6,397,847 B1 * 6/2002 Scarberry et al. ...... 128/206.24
6,581,602 B1 * 6/2003 Kwok et al. ........... 128/207.13
6,651,663 B1 * 11/2003 Barnett et al. ......... 128/205.25
6,748,949 B1 * 6/2004 Smaldone .............. 128/203.29

OTHER PUBLICATIONS

Copy of International Search Report for PCT/US04/36435, dated Dec. 19, 2005.

* cited by examiner

*Primary Examiner*—Teena Mitchell
*Assistant Examiner*—Andrew Bunin
(74) *Attorney, Agent, or Firm*—Darby & Darby

(57) ABSTRACT

Face masks for use in pressurized drug delivery applications, such as aerosol drug delivery systems, and a method of reducing aerosol deposition in the region of the eyes are presented. The face masks according to the various embodiments disclosed herein contain features that reduce the inertia of the aerosolized drug in perinasal areas. This results in a reduction in the amount of aerosolized drug that is deposited in the region of the eyes by inertial impaction, while at the same time, the features are constructed to maintain the flow of the aerosolized drug into the face mask so that the aerosolized drug is effectively delivered to the respiratory system of the patient.

33 Claims, 15 Drawing Sheets

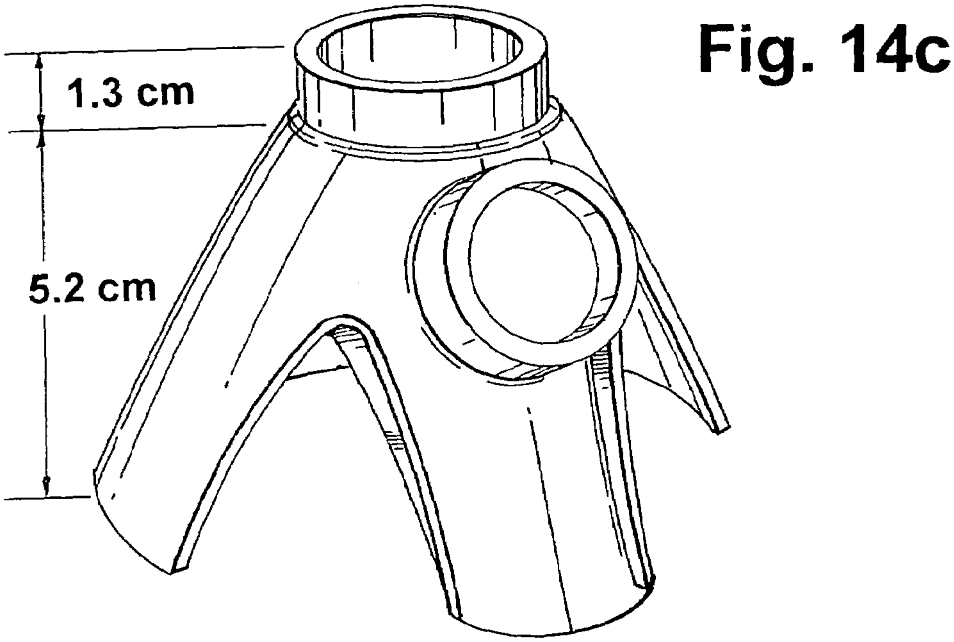
Fig. 14c
Fig. 14d
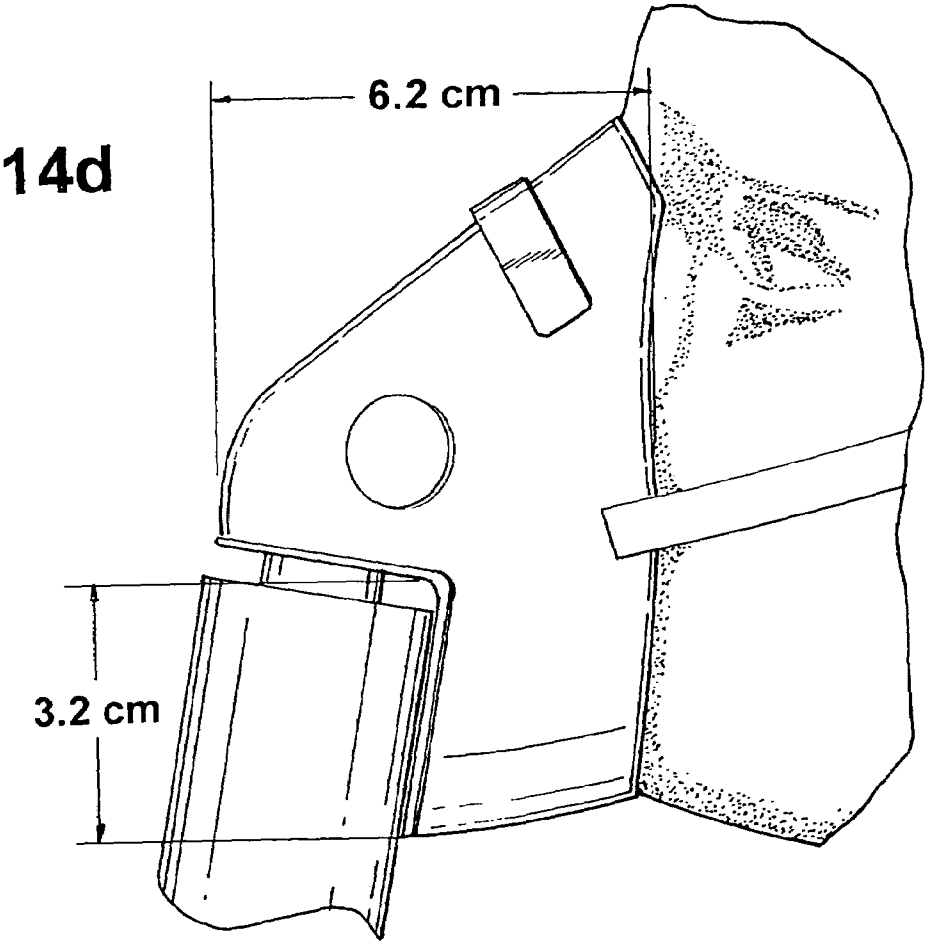

MIT Face Deposition Study Using Saline & Tc.99' Compressor the Data are Entered as Percent of Mean ± SE

| Mask Type | NEBULIZER | n | %I.M. | % FACE | % EYES | % BUDESONIDE EYES | % MASK | MMAD |
|---|---|---|---|---|---|---|---|---|
| Laerdal STD | LC PLUS | 6 | 6.70±0.76 | 2.11±0.32 | 1.45±0.31 | 1.68±0.32 | 1.06±0.14 | 6.6 |
| Lardal LEC | | 4 | 6.26±0.45 | 0.64±0.13 | 0.07±0.02 | 0.22±0.06 | 0.64±0.09 | 6.0 |
| Panda STD | | 4 | 5.56±0.62 | 0.79±0.11 | 0.34 0.08 | 0.48±0.06 | 1.06±0.24 | 6.2 |
| Panda LEC | | 4 | 5.23±0.26 | 0.56±0.06 | 0.06±0.01 | 0.20±0.03 | 1.22±0.14 | 5.1 |
| Panda LEC-MOD. | | 4 | 7.35±0.39 | 0.56±0.09 | 0.09±0.04 | 0.20±0.03 | 1.22±0.14 | 5.4 |
| Bubble STD | | 6 | 6.30±0.76 | 0.50±0.09 | 0.11±0.03 | 0.24±0.05 | 1.19±0.19 | 6.8 |
| Bubble Eyecut | | 4 | 6.01±0.60 | 0.56±0.09 | 0.10±0.02 | 0.24±0.03 | 1.20±0.19 | 4.5 |
| Origional P SEC | | 2 | 7.35±1.56 | 0.62±0.07 | 0.10±0.02 | 0.34±0.04 | 1.35±0.12 | 5.7 |
| Origional PP LEC | | 2 | 9.59±1.50 | 0.83±0.07 | 0.11±0.01 | 0.40±0.02 | 1.84±0.12 | 5.8 |
| Origional P SEC | MIST NEBULIZER | 2 | 5.03±0.25 | 0.76±0.56 | 0.12±0.01 | 0.43±0.04 | 1.72±0.10 | 8.5 |
| Origional PP LEC | | 2 | 4.84±0.63 | 0.83±0.11 | 0.12±0.01 | 0.44±0.06 | 1.54±0.28 | 8.0 |
| Salter STD | | 4 | 5.84±0.28 | 2.34±0.16 | 0.46±0.06 | 1.23±0.12 | 5.06±0.92 | 8.4 |
| Origional P SEC | NEBU TECH | 2 | 2.55±0.60 | 0.61±0.18 | 0.08±0.04 | 0.29±0.10 | 1.17±0.33 | 7.7 |
| Origional PP LEC | | 2 | 2.59±0.78 | 0.80±0.33 | 0.09±0.03 | 0.39±0.15 | 1.15±0.36 | 5.7 |
| Salter STD | | 3 | 1.93±0.28 | 1.70±0.22 | 0.35±0.05 | 0.93±0.13 | 1.56±0.28 | 7.6 |
| Origional PP LEC | AEROTECH II | 2 | 10.61±0.96 | 0.59±0.06 | 0.08±0.01 | 0.28±0.02 | 0.63±0.00 | 2.5 |

P = Prototype; PP = Prototype Painted
Marple Casscade ran for 2 min for MMAD

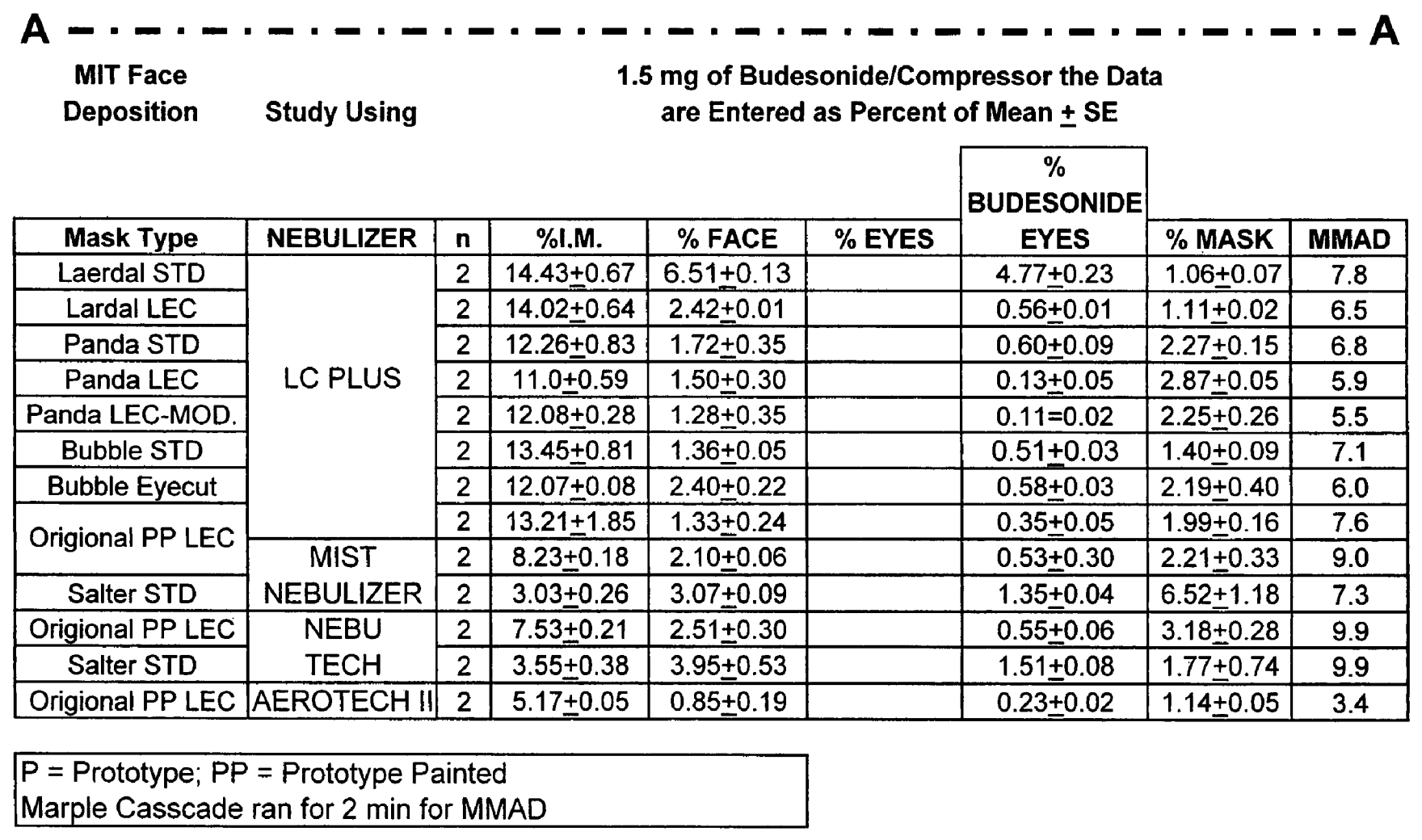

MIT Face Deposition Study Using 1.5 mg of Budesonide/Compressor the Data are Entered as Percent of Mean ± SE

| Mask Type | NEBULIZER | n | %I.M. | % FACE | % EYES | % BUDESONIDE EYES | % MASK | MMAD |
|---|---|---|---|---|---|---|---|---|
| Laerdal STD | LC PLUS | 2 | 14.43±0.67 | 6.51±0.13 | | 4.77±0.23 | 1.06±0.07 | 7.8 |
| Lardal LEC | LC PLUS | 2 | 14.02±0.64 | 2.42±0.01 | | 0.56±0.01 | 1.11±0.02 | 6.5 |
| Panda STD | LC PLUS | 2 | 12.26±0.83 | 1.72±0.35 | | 0.60±0.09 | 2.27±0.15 | 6.8 |
| Panda LEC | LC PLUS | 2 | 11.0±0.59 | 1.50±0.30 | | 0.13±0.05 | 2.87±0.05 | 5.9 |
| Panda LEC-MOD. | LC PLUS | 2 | 12.08±0.28 | 1.28±0.35 | | 0.11=0.02 | 2.25±0.26 | 5.5 |
| Bubble STD | LC PLUS | 2 | 13.45±0.81 | 1.36±0.05 | | 0.51±0.03 | 1.40±0.09 | 7.1 |
| Bubble Eyecut | LC PLUS | 2 | 12.07±0.08 | 2.40±0.22 | | 0.58±0.03 | 2.19±0.40 | 6.0 |
| Origional PP LEC | LC PLUS | 2 | 13.21±1.85 | 1.33±0.24 | | 0.35±0.05 | 1.99±0.16 | 7.6 |
| Origional PP LEC | MIST NEBULIZER | 2 | 8.23±0.18 | 2.10±0.06 | | 0.53±0.30 | 2.21±0.33 | 9.0 |
| Salter STD | MIST NEBULIZER | 2 | 3.03±0.26 | 3.07±0.09 | | 1.35±0.04 | 6.52±1.18 | 7.3 |
| Origional PP LEC | NEBU TECH | 2 | 7.53±0.21 | 2.51±0.30 | | 0.55±0.06 | 3.18±0.28 | 9.9 |
| Salter STD | NEBU TECH | 2 | 3.55±0.38 | 3.95±0.53 | | 1.51±0.08 | 1.77±0.74 | 9.9 |
| Origional PP LEC | AEROTECH II | 2 | 5.17±0.05 | 0.85±0.19 | | 0.23±0.02 | 1.14±0.05 | 3.4 |

P = Prototype; PP = Prototype Painted
Marple Casscade ran for 2 min for MMAD

Fig. 15B

FACE MASK FOR USE IN PRESSURIZED DRUG DELIVERY SYSTEMS

CROSS REFERENCE TO RELATED APPLICATIONS

The present application claims the benefit of U.S. patent application Ser. No. 60/515,382, filed Oct. 29, 2003, and U.S. patent application Ser. No. 60/566,117, filed Apr. 27, 2004, both of which are hereby incorporated by reference in their entirety.

BACKGROUND

1. Technical Field

The present invention relates to a mask and more particularly, to a face mask for use in delivering an aerosolized drug or the like to a patient.

2. Description of Related Art

Masks are commonly used in a wide range of applications and have widespread use in a number of medical settings. For example, masks are typically used in administering gases to a patient, e.g., an anesthetic agent, and more recently, masks have been increasingly used in drug delivery systems, including nebulizer drug delivery systems and metered dose inhalers using valved holding chambers (MDI/VHC). Nebulization is the application of a drug to a patient by means of an aerosol produced by a flow of gas. The aerosol and the drug are breathed in through the mask and are administered into the respiratory system of the patient as the patient inhales. The MDI/VHC creates its aerosol from the expansion of a volatile liquid into a gas within the VHC.

Nebulization is particularly used in the pediatric field as a means for delivering a drug or the like. In patients, such as young children, who have limited cooperation and attention span, the delivery of an aerosolized drug is carried out primarily with the use of a face mask. The face mask is placed over the nose and mouth of the patient, held in place by a caregiver or by using conventional straps or the like. The face mask is attached to an aerosol drug delivery device. In the case of nebulizers, the face mask is pressurized by the flow from the nebulizer and aerosol fills the mask becoming available for inhalation via the nose or the mouth. When the patient inhales, a negative pressure is applied to the face mask reservoir and the aerosolized drug is inhaled and enters into the respiratory system of the patient.

Metered dose inhalers are also used with face masks to disperse a drug to a patient. These devices dispense a predetermined amount of drug when activated and the patient is required to inhale in order to draw the aerosolized drug into the face mask reservoir and subsequently into the respiratory system of the patient.

Nebulizer drug delivery is different from drug delivery using a metered dose inhaler particularly in the degree of pressurization of the face mask. Metered dose inhalers can pressurize the mask to some degree, especially if aerosol is sprayed directly into the mask and a spacer is not used. A spacer is a device which is placed between the face mask and the source of aerosol (typically a bottle). Often, the spacer has one way valves and therefore is called a “valved holding chamber” (VHC). Face masks are used for both nebulizer drug delivery and for metered dose applications, but there are several associated shortcomings.

Nebulizers readily pressurize the mask and deliver more drug but leaks around the face are enhanced, resulting in increased facial deposition of the drug. Thus, leakage around the mask affects the performance of the particular device and in the case of nebulizers, leakage actually enhances the delivery of the drug; however, it is enhanced at the price of increased facial deposition and potentially local side effects. In order to effectively administer the aerosolized drug into the respiratory system of the patient, the face mask should cover the entire mouth and nasal openings of the patient.

The face mask is generally arranged so that it seats against the cheeks of the patient and extends across an upper portion of the bridge of the patient’s nose. Because the bridge of the nose is elevated relative to the rest of the patient’s face, e.g., cheeks, the upper portion of the face mask is slightly elevated relative to surrounding portions of the face mask which extend across the cheeks and under the mouth of the patient. This occurs even when the patient attempts to produce a tight seal between the mask and the face. For nebulizers, this produces certain leakage areas where the aerosolized drug can be discharged underneath the face mask and into the atmosphere. Because of the design of face masks and their above-described placement over the face, leakage is universally present in the perinasal areas on either side of the nose. This results in a jet of leaked aerosol being oriented and deposited directly into the eyes of the patient. In other words, aerosol is discharged underneath the face mask in these perinasal areas and flows directly towards the patient’s eyes and unfortunately, many of the conventional masks are constructed in such a manner that the leaks that do occur are characterized as being high powered leaks (high kinetic energy) due to the high velocity that the fluid has as it flows underneath the mask and along the face directly into the eyes.

This may lead to several undesired side effects. For example, deposition of the leaked aerosolized drug may be associated with direct trauma to the eyes and associated structures. As leakage occurs, these organs are exposed to the aerosolized drug. There is speculation that the risk of developing cataracts increases as a result of aerosolized drugs being directly deposited in the eyes of the patient. At the very least, leakage of aerosolized drugs causes discomfort as the aerosol, traveling at a great velocity, is discharged underneath the face mask and deposits in the perinasal areas, including the eyes. In addition, leaks of certain aerosols can cause dermatological problems in some patients due to an adverse reaction between facial skin and the aerosol. Other undesirable conditions may result from having the aerosolized drug leaking and being deposited onto the face.

The disadvantages associated with conventional mask constructions are readily apparent by viewing FIGS. 1, 1*a* and 2. FIG. 1 is a front perspective view of a typical face mask 100 (that is commercially available from Laerdal Medical Corporation of Wappingers Falls, N.Y.). While, the face mask 100 is illustrated as being worn by an adult in FIGS. 1 and 1*a*, it will be understood that face mask 100 is designed to be worn by small children and finds particular application in pediatric care where the patient is unable or uncooperative in the administration of the drug. The face mask 100 has a body 102 including a peripheral edge 104 which is intended to engage a face of a patient. The body 102 defines a face mask reservoir in which the patient’s nasal openings and mouth are in communication. The body 102 is typically made of a flexible material, such as a thermoplastic, e.g., a PVC material. The body 102 has a central opening 106 defined in part by an annular flange-like member 108 which extends outwardly from an outer surface 109 of the body 102. During use, the member 108 is coupled to other components of a drug delivery system (not shown) to permit delivery of the aerosolized drug. The opening 106 serves as a means for delivering the aerosolized drug to the patient.

Depending upon the type of drug delivery assembly that is being used, e.g., a metered dose inhaler or a nebulizer system, the opening 106 receives the aerosolized drug as it is transported to the face mask reservoir defined by the body 102. The breathing action of the patient causes the aerosolized drug to be inhaled by the user and introduced into the patient's respiratory system.

As previously mentioned, one of the deficiencies of the face mask 100 is that leakage areas form around the peripheral edge 104. More specifically, the peripheral edge 104 does not form a complete seal with the face of the patient and accordingly, leakage flow paths 107 with high local velocities are formed at certain areas along the periphery of the face mask 100, especially in perinasal areas 105. In fact, maneuvers to reduce leaks along edge 100 may increase the velocity of leaks in perinasal areas 105. The perinasal areas 105 are particularly prone to the formation of leaks and this results in the aerosolized drug being discharged directly into the eyes and the associated structures. As previously mentioned, there are at least two different types of aerosolized drug delivery systems that are commonly used with a face mask, such as face mask 100. One type utilizes a pressurized metered dose inhaler (MDI/VHC) and the other type utilizes a jet nebulizer.

FIGS. 1 and 1*a* illustrate the face mask 100 as part of an aerosol drug delivery system that utilizes a jet nebulizer 200. The nebulizer 200 is operatively coupled to a compressor (not shown) which generates compressor air through the nebulizer 200. The nebulizer 200 has a body 210 which is coupled to a hose 220 that connects to the compressor at a first section 222 and is constructed so that compressor air flows therethrough. The drug to be delivered is stored in the body 210 using conventional techniques. A second section 224 of the nebulizer 200 communicates with the face mask reservoir so that the aerosolized drug is delivered into the face mask reservoir. The body 210 can include conventional venting and filtering mechanisms.

During aerosol generation, compressor air flows through the body 210 and into the face mask reservoir. This results in pressurization of the face mask 100 and also facilitates leaks at various locations (especially, the perinasal areas) around the face mask 100 with enhanced facial deposition being realized. Once the face mask 100 becomes fully pressurized, excess compressor air (including the aerosolized drug) is vented through an exhaust vent. This results in some of the aerosolized drug being lost into the surrounding environment. The face mask 100 is partially depressurized when the patient inhales but then as soon as the patient stops inhaling and exhales, the face mask 100 is again fully pressurized because of the continuous flow of the compressor air.

When the face mask is placed on a patient, an imperfect seal between the peripheral edge 104 of the face mask 100 and the patient's face typically results due to a number of factors (including face contour of the specific patient). This occurs for small children, children, and adults. The leaks that occur due to the pressurization of the face mask 100 result in the aerosolized drug flowing according to flow paths indicated by arrows 107. These leaks occur around the nose (perinasal areas), the cheeks and at the chin of the patient. It has also been found that the degree of pressure applied to the mask in an attempt to improve the seal between the face mask and the face does not necessarily improve and may in fact worsen the leakage of the aerosolized drug in the perinasal areas when the patient inhales and draws the aerosolized drug into the face mask reservoir. During therapy, local pressure on standard masks may facilitate high local velocities that can lead to eye deposition. For example a caregiver pressing on the mask can seal leaks along the cheeks but promote leaks around the eyes. The leakage of the aerosolized drug in the perinasal areas results in the aerosolized drug being discharged towards the eyes of the patient at high velocities due to the high kinetic energy of the fluid. This is less than ideal as it may cause discomfort at the very least and may also lead to other medical complications due to the drug being discharged into the eyes of the patient.

Eye deposition is thus particularly a problem for those drug delivery systems that exert greater pressure on the face mask and/or maintain the face mask reservoir under pressure. Because pressurization of the face mask 100 plays an important role in a nebulizer drug delivery system and nebulizers have become an increasingly popular means for delivering an aerosolized drug to a patient in such a manner that exhibits a high degree of pressurization in the face mask, the present applicant has studied the amount of eye deposition which occurs when face mask 100 is used in combination with the nebulizer 200 since the face mask pressurization associated with nebulizer use promotes a higher level of leakage around the eye region.

FIG. 2 is a gamma camera image obtained using a simulator face as part of a radiolabel face deposition study carried out using the face mask 100 of FIG. 1 in combination with the nebulizer 200. In these studies, the face mask 100 was attached to a breathing emulator (not shown) which simulated the breathing pattern of a particular type of patient. The breathing emulator includes a three dimensional, contoured bench model face to which the face mask 100 was attached. A filter was placed in the mouth of the bench model face so as to best determine the inhaled mass (actual quantity of aerosol inhaled) as the filter represents the final path of the particles passing into patient.

By using nebulized radiolabeled saline acting as a surrogate drug in the nebulizer 200, the deposition pattern of the particles can easily by determined. FIG. 2 represents deposition following tidal breathing (also referred to as tidal volume) of 50 ml with a minute ventilation of 1.25 liters/min, a pattern typical of a small child. Airflow from the nebulizer 200 is 4.7 liters/minute and therefore the face mask 100 is highly pressurized. Under these conditions, aerosolized drug leaks from the mask at various points on the face, as evidenced by the concentrated areas appearing in the image. As seen in FIG. 2, there is a high level of deposition in the area of the eyes of the patient and there is also a high level of deposition in the chin and jaw areas of the patient. It will be appreciated that other aerosol drug delivery systems which cause the face mask to become pressurized will likely generate similar data showing eye deposition of the aerosolized drug.

While face masks having been developed with venting mechanisms to cope with the pressurization requirements of a nebulizer or the like, these face masks still suffer from the disadvantage that they have constructions that not only permit aerosolized drug to be discharged in the perinasal areas but more importantly, the aerosolized drug is discharged at high velocities toward the eyes due to the imperfect interface between the face mask and the face. In effect, this imperfect interface "funnels" the aerosolized drug so that the aerosolized drug exits the face mask at a high velocity toward the eyes.

What is needed in the art and has heretofore not been available is a face mask which reduces the inertia of the aerosolized drug in the perinasal areas thus reducing deposition in the region of the eyes by inertial impaction, while maintaining flow of the aerosol into the face mask so that the aerosolized drug is effectively delivered to the respiratory system of the patient. The exemplary face masks disclosed herein satisfy these and other needs.

SUMMARY

In one exemplary embodiment, a face mask for use in pressurized drug delivery applications, such as aerosol drug delivery systems, and a method of reducing aerosol deposition in the region of the eyes are presented. The face masks according to the various embodiments disclosed herein contain features that reduce the inertia of the aerosolized drug in perinasal areas. This results in a reduction in the amount of aerosolized drug that is deposited in the region of the eyes by inertial impaction, while at the same time, the features are constructed to maintain the flow of the aerosolized drug into the face mask so that the aerosolized drug is effectively delivered to the respiratory system of the patient.

According to one exemplary embodiment, the face mask has a body having a bottommost edge or surface for placement against a face of a patient. A nose bridge section is formed in an upper section of the mask body to seat against the nose of the patient when the mask is placed against the face during the application. The body has a pair of eye vents formed therein, with one eye vent being formed on one side of the nose bridge section and the other eye vent being formed the other side of the nose bridge section. When the face mask is worn by the patient, the eye vents are generally orientated underneath the eyes of the patient. The eye vents are thus eye cut outs or openings formed along the peripheral edge of the mask body by removing mask material. The present applicant has found that opening the face mask at the sites of the greatest risk (i.e., the eyes), where aerosolized drug flow is not desired, compels and ensures the local reduction of particle inertia at the sites most at risk of facial damage and irritation. The excisions in the face mask that serve as eye vents thus minimize the local velocity and particle inertia such that the particles do not impact on the surface of the face and eyes and actually pass over the face and eyes without deposition thereon as shown by arrows in FIG. 3. This results in a substantial reduction of deposition in the region of the eyes compared to conventional face masks.

The eye cut outs or openings can be formed in any number of different sizes and any number of different shapes (e.g., semicircular) based upon the performance characteristics (i.e., inhaled mass value, facial deposition amount, etc.) that are desired in the application of the aerosolized drug. The eye vents can also be used in combination with a supplemental vent that is also formed in the face mask body. For example, the supplemental vent can be in the form of an opening that is formed in the mask in a lower chin section near the peripheral edge. By providing eye vents in the face mask, a face mask is provided that substantially alleviates or eliminates the discomfort and potential harmful consequences that are associated with face masks that have leaks in the perinasal areas which result in the aerosolized drug being "funneled" between the peripheral edge of the face mask and the face and causing the aerosolized drug to flow at great velocities into the eyes of the patient.

Moreover, by optimizing the distance from the face to a point of insertion of the nebulizer within a connection portion of the mask, a reduction in the inertia of the aerosolized drug in the perinasal areas is realized as well as across the face and this results in a reduction in the amount of aerosolized drug deposited on the face, including in the eye regions.

Further aspects and features of the present invention can be appreciated from the appended Figures and the accompanying written description.

BRIEF DESCRIPTION OF THE DRAWINGS

FIGS. 14A–D illustrate a number of different face mask embodiments showing nozzle insertion distances that are measured between the nebulizer and the facial surface;

FIGS. 15A–B are a Table comparing drug delivery and facial deposition data obtained from testing a set of the exemplary face masks disclosed herein;

DESCRIPTION OF PREFERRED EMBODIMENTS

Additional details relating to the present invention are disclosed in commonly assigned U.S. Pat. No. 6,748,949, issued Jun. 15, 2004, and which is hereby incorporated by reference in its entirety.

It will also be understood that while the present face masks according to the present invention are particularly suited for young children; the present face masks and the teachings disclosed herein are also applicable to use with adults. In other words, the above mentioned disadvantages that are associated with conventional face masks apply not only to child sized masks but also apply to adult sized face masks and therefore, undesired drug deposition occurs in adult face masks. Accordingly, the face masks disclosed herein that include eye vents and/or optimization of other mask features are not limited to child mask constructions but apply equally to other face masks, including adult face masks.

Figure 1:
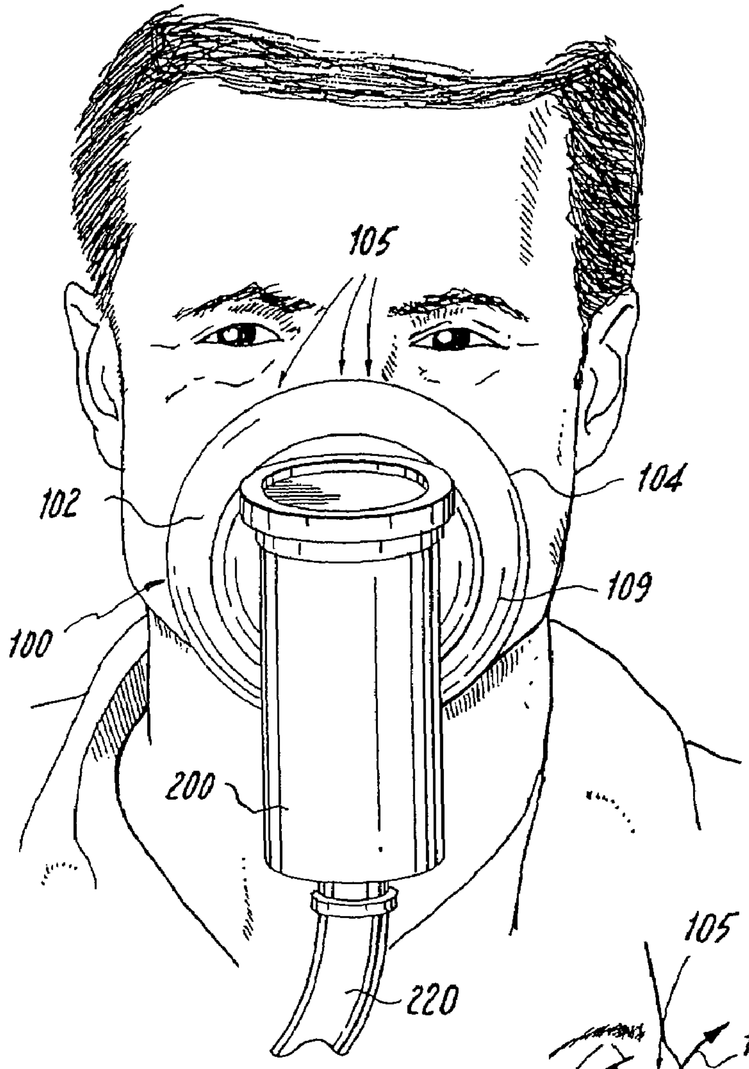
FIG. 1 is a front elevational view of a conventional face mask shown as part of a nebulizer drug delivery system and in a typical administering position on a patient such that it is arranged so that the mask covers the nose and mouth of the patient.
Figure 1A:
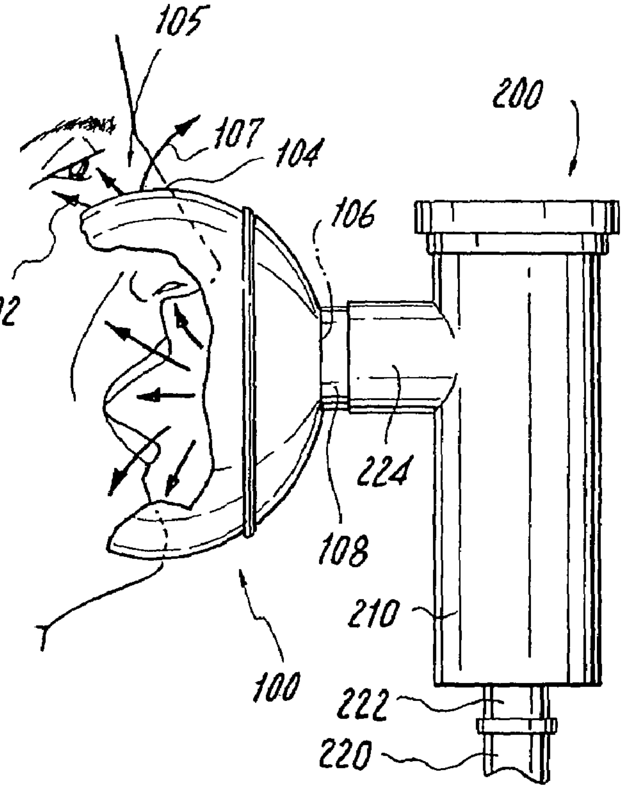
FIG. 1*a* is a side elevational view of the face mask of FIG. 1 with a section being cut-away to illustrate the flow paths of the aerosolized drug when the face mask is worn by a patient.
Figure 2:
FIG. 2 is an image obtained using a gamma camera scan of a face model as part of a radiolabel face deposition study carried out using the conventional face mask of FIG. 1 illustrating particle deposition (aerosol drug) occurring in response to a pediatric pattern of breathing (tidal volume 50 ml, frequency of breathing 25 breaths per min, duty cycle 0.4)
Figure 3:
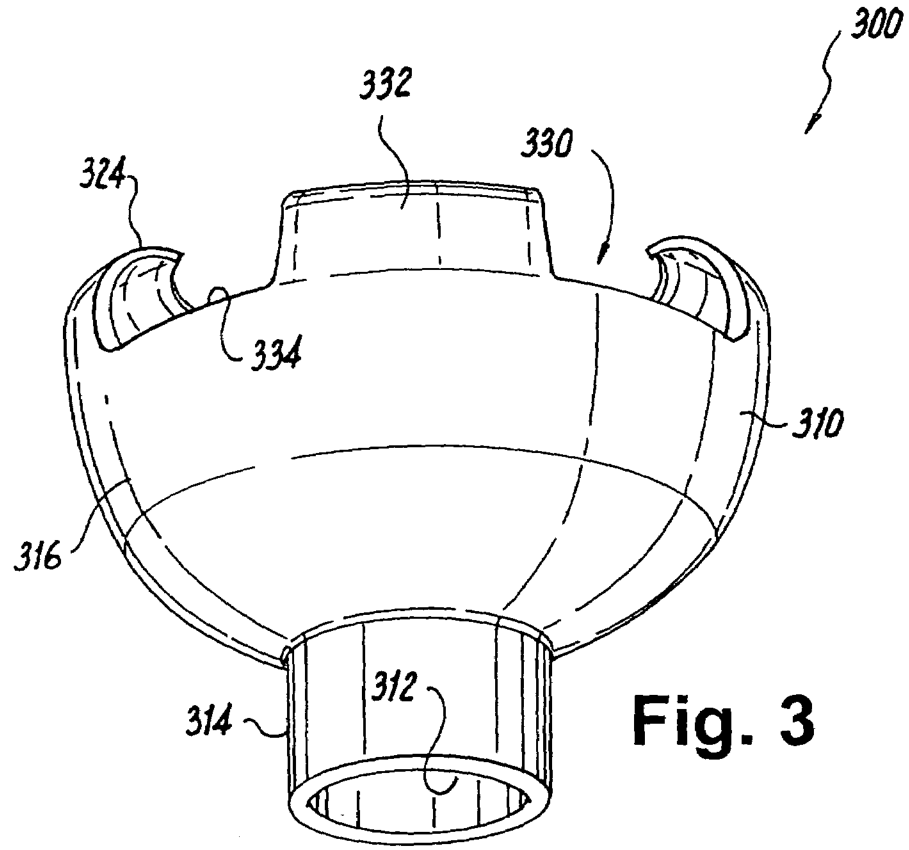
FIG. 3 is a top perspective view of a face mask according to a first exemplary embodiment for use as part of a nebulizer drug delivery system and prior to being placed in a typical administering position on a patient.
Figure 4:
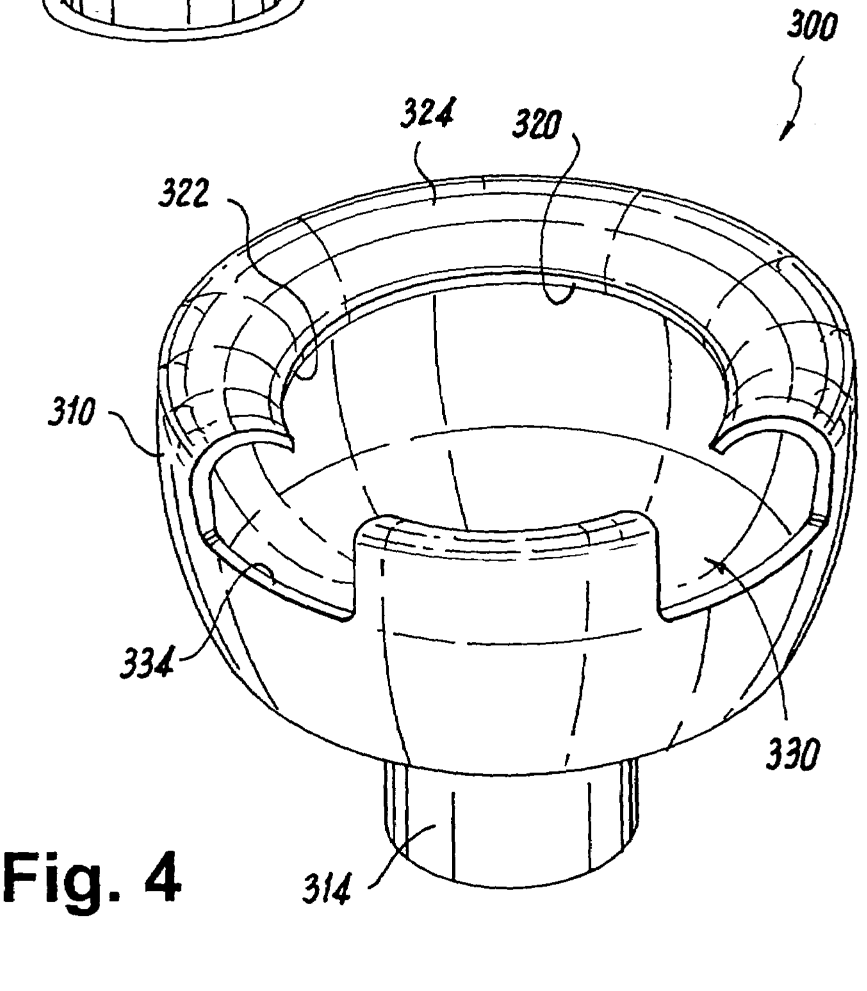
FIG. 4 is a bottom perspective view of the face mask of FIG. 3.
Figure 5:
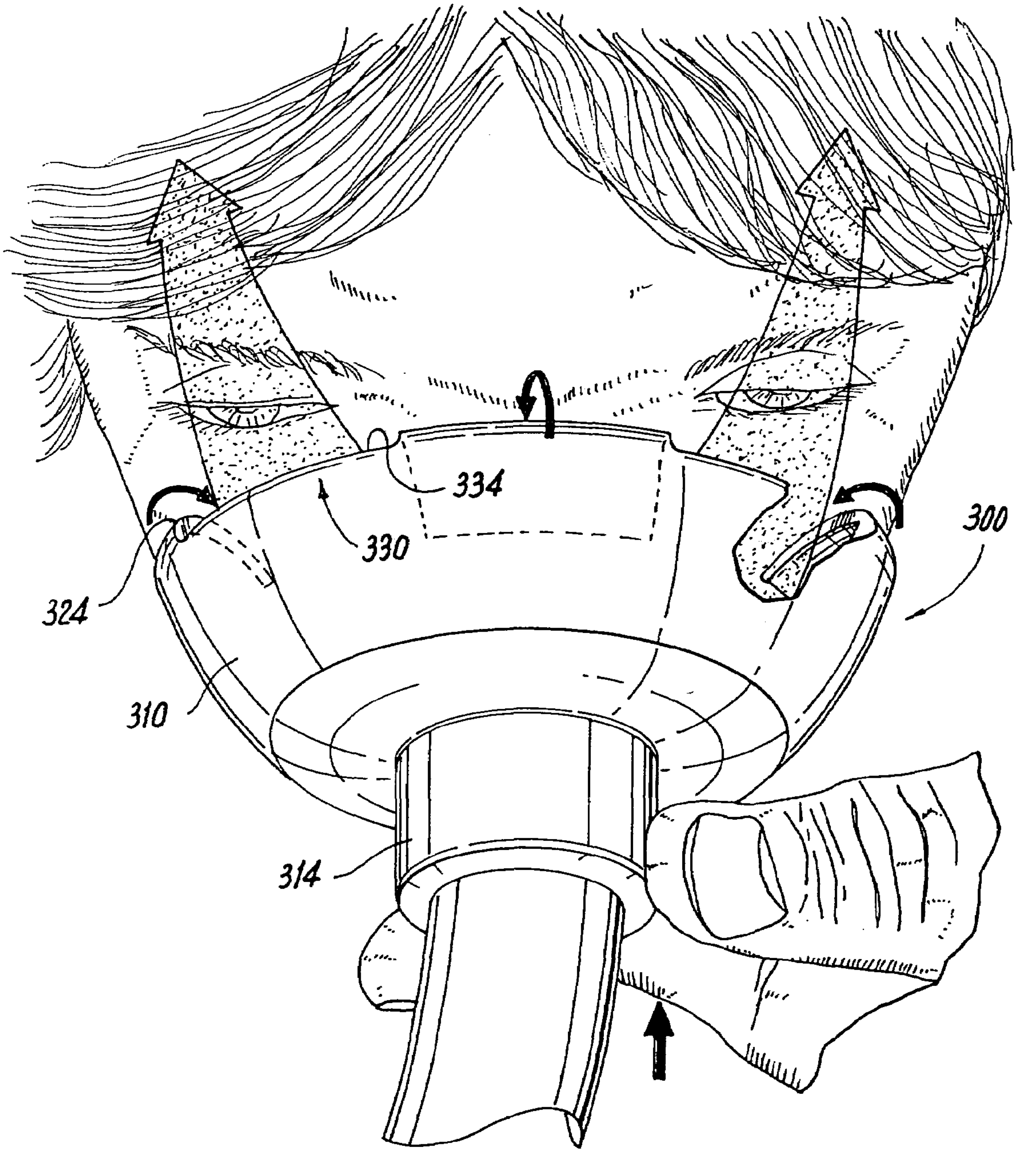
FIG. 5 is a perspective view of the face mask of FIG. 3 being placed in the typical administering position on the patient with the partially folded body being compressed and folded resulting in a reduction in size of the eye vents.

Now turning to FIGS. 3–5 in which a face mask 300 according to a first exemplary embodiment is shown and is for use as a part of a nebulizer drug delivery system. FIGS. 3 and 4 show the face mask 300 prior to being placed in a typical administering position on a patient where it is arranged so that the mask covers the nose and mouth of the patient, while FIG. 5 shows the mask 300 in the typical administering position.

In one embodiment, the face mask 300 is formed of a flexible polymeric material and is commercially available from Laerdal and is marketed as a pediatric silicone mask used for resuscitation purposes. More specifically, the mask 300 is formed of a body 310 that is not overly rigid but rather is compressible due to being formed of a flexible polymeric material and therefore, when the mask 300 is placed against a face of the user, the body 310 deforms slightly. It will be appreciated that the mask 300 illustrated is merely exemplary and depicted only for purposes of illustration and there are a number of other flexible pediatric face masks that can be used in accordance with the present invention. The body 310 has a first central opening 312 defined in part by an annular flange-like member 314 which extends outwardly from an outer surface 316 of the body 310. The body 310 is formed of a flexible material such that it readily deforms or compresses when a force is applied thereagainst as when the user applies the face mask 300 to the face of the patient.

The body 310 extends outwardly from the flange-like member 314 and then folds (curls) inwardly and underneath to a second central opening 320 that is placed over the mouth of the patient. An edge 322 of the body 310 defines the second central opening 320 and because of the folded or arcuate nature of the body 310, the edge 322 is not the bottommost portion of the body 310. Instead, a bottommost portion 324 of the body 310 is formed by the folded or curved section of the body 310. It is this section 324 that makes initial contact with the face of the patient as shown in FIG. 5 and because the body 310 is deformable, the body 310 deforms and slightly collapses as the user presses the mask 300 against the face. As shown in FIG. 5, the mask 300 actually folds even more at the bottommost portion 324.

In this embodiment and as opposed to a more rigid face mask, the mask 300 does not include a clearly defined peripheral edge that seats against the face of the patient but rather the portion that sits against the patient's face is the folded portion of the face mask 300.

Similar to the other embodiments, the face mask 300 includes a pair of eye vents 330 that are formed on each side of a bridge section 332 of the body 310 by removing the mask material in this location. FIGS. 3–5 illustrate the eye vents 330 according to one embodiment and having one exemplary shape with each eye vent 330 having an inner edge 334 and the eye vent 330 being constructed so that it extends from the inner edge 334 to the second central opening 320. The eye vent 330 is thus formed in the folded bottommost portion 324 of the body 310. The eye vent 330 can have any number of different shapes, such as oval, square, rectangular, oblong, triangular, etc., since the shape is not critical so long as the eye vents provide an adequate outlet for venting the drug.

When the face mask 300 is placed against the face during an application, as shown in FIG. 5, the body 310 compresses somewhat with the bottommost portion 324 being further folded over (i.e., collapsing inward). The result of this is that the distance between the inner edge 334 and a bottommost section 324 of the face mask 300 decreases as can be seen. In other words, the area of the open eye vent 330 decreases in a corresponding fashion due to this folding action. As seen in FIG. 5, each eye vent 330 extends from and is open from the bridge section 332 to another opposing edge or surface associated with the bottommost edge of the face mask 300. However, the eye vent 330 is still open even though the mask 300 has been further folded over itself and compressed since there is still an opening formed between the inner edge 334 and the face of the patient. In other words, a slit or opening is present between inner edge 334 and the patient's face in a location generally underneath one eye of the patient and this permits the desired venting effect to take place and all of the advantages noted hereinbefore are realized even in this embodiment where the face mask 300 is of a flexible type that compresses along the face when pressed thereagainst.

The eye vents 330 vent aerosolized drug flow from the mask into the region of the eyes. Contrary to one's initial inclination of not providing vents directly in the area where aerosolized drug flow is not desired, the Applicant has discovered that the provision of eye vents 330 in the eye region actually greatly improves the performance and the safety of the face mask 300 by altering the flow characteristics of the aerosolized drug in the eye region (i.e., the perinasal areas). One way of understanding the advantages provided by the eye vents 330 is by investigating the particle inertia of the fluid in the area of interest, namely the region of the eyes. In general, the deposition of particles is related to the diameters of the particles (hereinafter "a"), the velocity of the particle movement imparted by the local flow through the leak (hereinafter "U") in the face mask, and the local geometry between the face mask and the face (hereinafter "D"). All of these factors can be described together via local Stokes numbers (hereinafter "Stk"). Stk is dimensionless term that is related to particle inertia. The greater the inertia of particles, the greater the tendency for these particles to impact the face (eyes) and deposit on the face. Equation (1) sets forth the general relationship between the various variables:

$$Stk\alpha[a^2(U)]/D \quad \text{(Equation 1)}$$

where D can be related to U as set forth in Equation (2):

$$U\alpha Q/D \quad \text{(Equation 2)}$$

where Q is the volume rate of flow out of the area of the mask that exhibits leakage. It will be appreciated that increases in local diameter of the site of the leak, decreases local linear velocity. That is, the particle inertia is affected by the diameter of the particles (a), the local velocity of the fluid (U) and has an inversion relationship relative to the local diameters (D).

The exemplary face mask 300 reduces Stk by increasing D which results in a decrease in U (Equation 2) and Stk. Further effects on U occur via mask decompression as reducing pressure within the mask further reduces Q. The latter accomplished via the opening D, which acts as a vent.

The face mask 300 provides a face mask where aerosol flow into the face mask is maintained (which is necessary for effective drug delivery), while at the same time, the construction of the face mask 300 reduces the deposition of aerosol in the region of the eyes and the rest of the face by opening the face mask 300 in the region of the eyes. Opening the face mask 300 at the sites of the greatest risk and at the very locations where aerosolized drug flow is not desired (the eyes) compels and ensures the local reduction of particle inertia at the sites most at risk of facial damage and irritation. Advantageously, the provision of eye vents 330 reduces particle velocity by increasing the space between the mask (increased Stokes Diameter (D)) and further, by decompressing the face mask reservoir (the area between the face and the inner surface of the face mask 300 when it is worn), the pressure within the face mask reservoir is reduced and this minimizes linear flow to the eyes (i.e., variable (U) of Equation 2). It will be understood that the local Stokes numbers are merely a tool to describe the advantages of the present face masks and in no way limit the scope of the present face masks as the principle can be understood by other means.

The wide excisions in the face mask 300 that serve as the eye vents 300 minimize the local velocity and particle inertia such that the particles (i.e., the aerosolized drug) do not impact on the surface of the face and eyes and actually pass over the face and eyes without deposition thereon. Accordingly, the eye vents 300 are formed generally underneath the eyes (while leaving the bridge section of the face mask in tact) in order to obviate the high pressure effects that were previously observed at the bottommost portion 324 of the face mask 300 due to the aerosolized drug escaping in this region at high velocities. By forming eye vents 330 by removing sections of the face mask 300, including sections of the bottommost portions 324 thereof, the interface between the bottommost portion 324 and the face is eliminated in this region and therefore, aerosolized drug is no longer “funneled” out of the mask 300 at the perinasal areas at great velocities. Thus, low velocities in this region are ensured independent of other multiple uncontrollable variables (pressure of the mask on the face, nebulizer flow into the mask) and deposition is always minimized.

Thus, the face mask 300 enhances the safety performance of the face mask by reducing the velocity of the aerosolized drug as it vents from the face mask 300 due to the face mask/face interface being obviated in the eye region. In this embodiment, the eye vents 330 are of reduced dimensions compared to other embodiments.

Since the excision of more and more mask material to form the eye vents 330 can serve to weaken the overall structural rigidity of the face mask 300, the eye vents 330 can be formed such that they each have a reinforcing member (not shown but similar to those disclosed in the previously incorporated patent application), which serves to reinforce the structural rigidity of the face mask 300 and ensure the robustness of the face mask 300. The reinforcing member is thus preferably formed around a inner edge 334 and other edges that define the eye vents 330 so as to increase the structural rigidity in the region of the eye vents 330. This ensures that the eye vents 330 substantially maintain their shape and form when the face mask 300 is placed on the patient’s head and pressure is applied to produce some type of seal between the face mask 300 and the face.

The reinforcing member can be any number of structures that either can be integral to the face mask 300 itself or can be later attached and secured to the face mask 300 after it has been fabricated and the eye vents 330 have been formed. For example, the reinforcing member can be in the form of a reinforced rigid, plastic piece that is securely attached to the face mask 300 using conventional techniques, such as using an adhesive, bonding, etc. By incorporating a rigid element into the face mask construction, the region of the face mask 300 that includes the eye vents 330 is less likely to deform or collapse but rather remains well defined during use of the face mask 300. The reinforcing member can also be in the form of a metal bushing that is attached to the face mask 300 using conventional techniques, such as those disclosed above. Further, the reinforcing member can be integrally formed with the rest of the face mask 300 when the face mask 300 is fabricated. For example, the reinforcing member for each eye vent 330 can be introduced into a mold and then the face mask 300 is formed therearound such that the reinforcing members are integral with the face mask 300. It will also be appreciated that if the face mask 300 is formed using a molding process, two or more different materials can be used to form the reinforced face mask in that one material can be used to form the reinforced members and another material can be used to form the rest of the face mask.

In yet another embodiment, the exemplary face mask 300 has a supplemental vent (not shown) formed in the face mask 300 for decompressing the face mask 300 and also for modifying the flow of the aerosolized drug that flows underneath the face mask 300 (especially in the perinasal areas) during a normal application when the face mask is placed against the face. The exemplary vent is a generally circular shaped opening; however, the shape of the vent is not critical. The vent is formed in the face mask body 310 at the 6 o’clock position. In other words, the vent is generally formed in the chin area of the face mask 300. The peripheral edge extends completely around the face mask 300 and therefore the vent is formed slightly away from the patient’s face. This is desirable as the vent serves to discharge aerosol and therefore, it is preferred to direct the aerosol downward and away from the patient’s face. The dimensions of the vent can be varied depending upon a number of factors, including the precise application, the size of the face mask, etc., so long as the vent has sufficient dimensions that permit a desired amount of the aerosolized drug to be inhaled by the patient, while at the same time, the face and eye deposition is reduced.

While the vent does serve to reduce aerosol deposition in the facial areas and also serves to decompress the face mask 300, the Applicant realized that (1) even those face mask with vents still have leaks between the face mask and the face (especially the perinasal areas thereof) which permits aerosolized drug to vent and (2) to increase the safety of face masks, it is more desirable to control the flow characteristics of the aerosolized drug that is discharged in the perinasal areas. Based on this information, the Applicant constructed a face mask that reduces face and eye deposition by modifying the flow characteristics of the aerosolized drug in the perinasal areas.

It will be appreciated that the provision of eye vents (of varying dimensions) in the face mask not only maintains an acceptable inhaled mass (and in most cases, results in an increase in the inhaled mass) but more importantly, the eye vents serve to modify the flow characteristics of the aerosolized drug (i.e., reduce the particle inertia of the aerosolized drug) in such a manner that results in increased safety since the high local velocities of the escaping aerosolized drug in the region of the eyes that plagued conventional face mask constructions is eliminated. In other words, the kinetic energy of the aerosolized drug in the region of the eyes is reduced by controlling the velocity of the aerosolized drug in the region of the eyes.

In the pediatric population, an inhaled mass value of about 4% is considered efficient for a drug delivery system. The low percentages are inherent to drug delivery systems in pediatrics because a large amount of the drug is wasted due to the drug either being vented from the mask as well as being trapped in the nebulizer or the like. The quantities deposited on the face and the eyes are low on a percentage basis but quite high on a drug delivery basis and thus it will be appreciated that facial and eye deposition in such pressurized drug delivery systems is a matter that deserves attention as it can lead to patient discomfort and can potentially lead to more serious complications, especially with the eyes.

One other advantage of the forming eye vents in a face mask that is intended for use with a pressurized drug delivery system, such as a nebulizer, is that existing face masks can easily be retrofitted by simply forming the eye vents in the region of the eyes using conventional techniques, such as a cutting process or any other type of process that is capable of removing or excising the face mask material along distinct lines to form the eye vents.

The present applicant has recognized that certain drug delivery systems, particularly nebulizer drug delivery systems, enhance facial and eye exposure to aerosols. Nebulizer aerosol delivery utilizing face masks pressurizes the face mask and facilitates leaks at various points around the face mask with enhanced facial deposition. Maneuvers that reduce this pressurization reduce the leak and concomitant deposition. By incorporating eye vents into the face mask, the shortcomings of conventional face masks have been essentially eliminated. The eye vents act to reduce particle inertia in the region of the eyes Based on the data displayed on the images and quantified in the present Tables, the incorporation of eye vents can cause a substantial reduction in the amount of aerosolized drug that was deposited in the region of the eyes. It will be appreciated that the size and cross-sectional shape of the eye vents may be altered and optimized to minimize leak and maximize drug delivery. The size of the eye vents should be tailored so that the inhaled mass value is within acceptable ranges for the given application.

It will be understood that any of face masks disclosed herein can be used in any number of applications where the face mask is pressurized by a fluid to such a degree that pressurization in the face mask results in leaks being formed around the face mask. Preferably, the face mask is used in those applications where it is desirable to preserve inhaled mass values. In other words, the use of the face mask should allow a sufficient amount of the aerosolized drug to flow into the face mask reservoir and then subsequently into the respiratory system of the patient.

Eye vents can be incorporated into a vast number of medical face masks that are intended for use in drug delivery systems or the like. Furthermore, the use of any of the exemplary face masks is not limited to only aerosol drug delivery systems. It will be appreciated that the face mask can be used in other types of fluid delivery systems having the same or similar characteristics as the discussed aerosol drug delivery system, e.g., pressurization of the mask and leakage, etc. While a number of the illustrations and the experimental data are directed to use of the various face masks in pediatric applications, it will be understood that the face masks according to the present embodiments can be used in other applications besides pediatric applications. For example, the face masks can be worn by adults to administer an aerosolized drug, etc.

Figure 6:
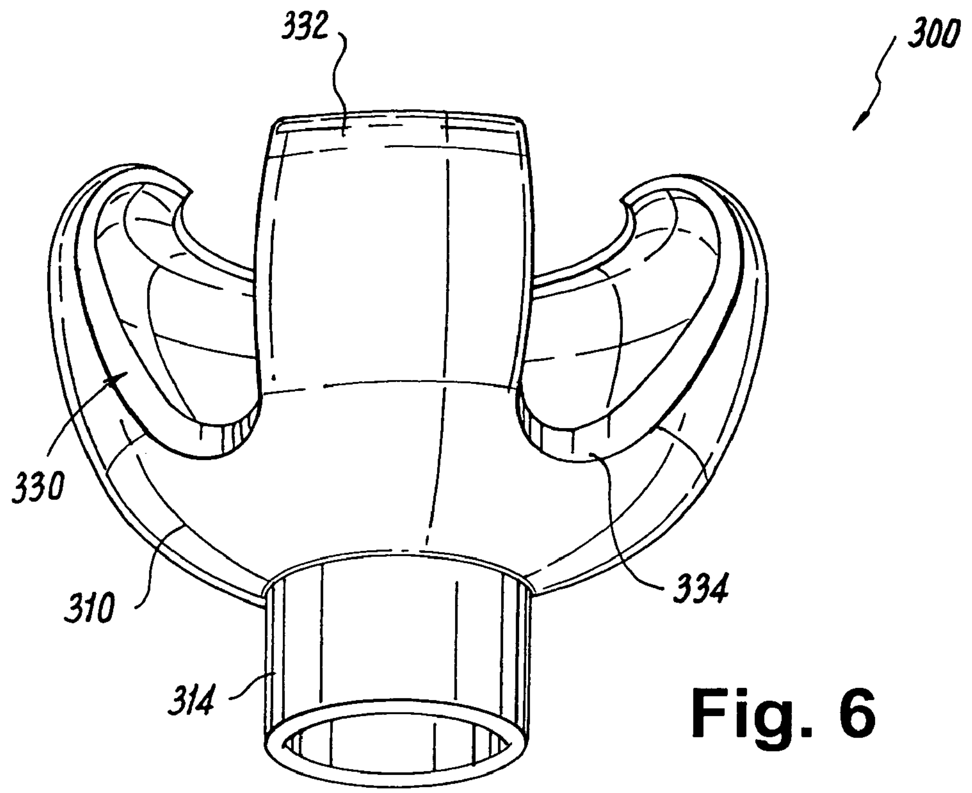
FIG. 6 is a top perspective view of a face mask according to a second exemplary embodiment for use as part of a nebulizer drug delivery system and prior to being placed in a typical administering position on a patient.
Figure 7:
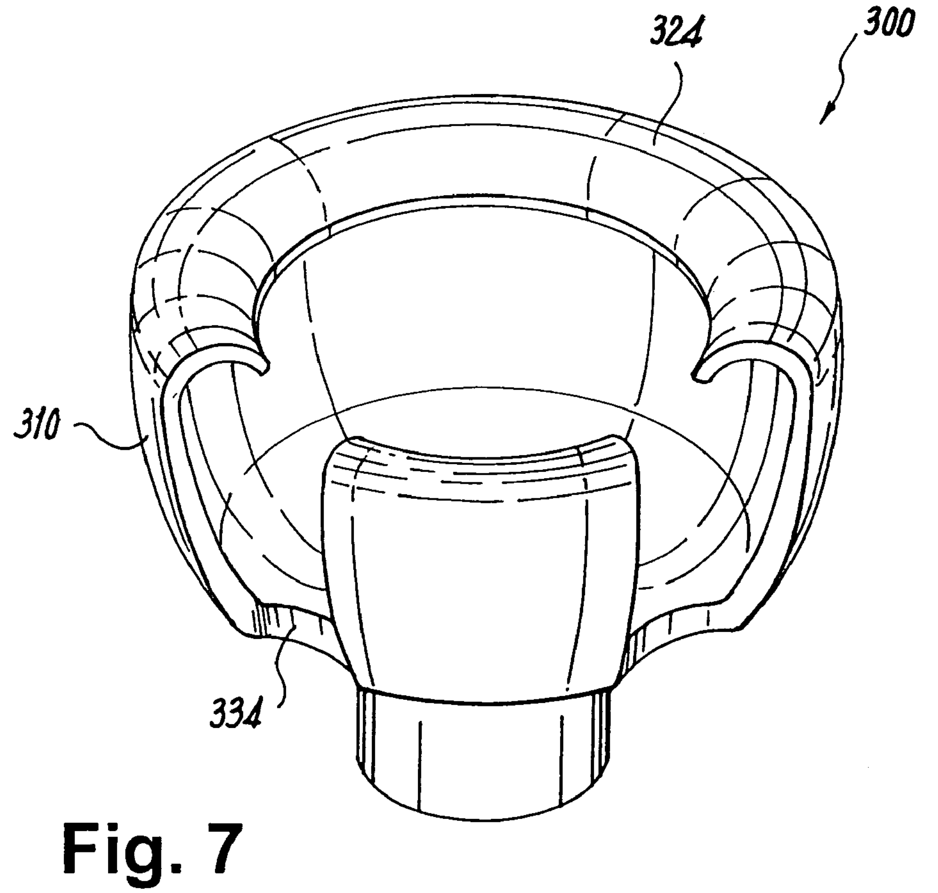
FIG. 7 is a bottom perspective view of the face mask of FIG. 6.
Figure 8:
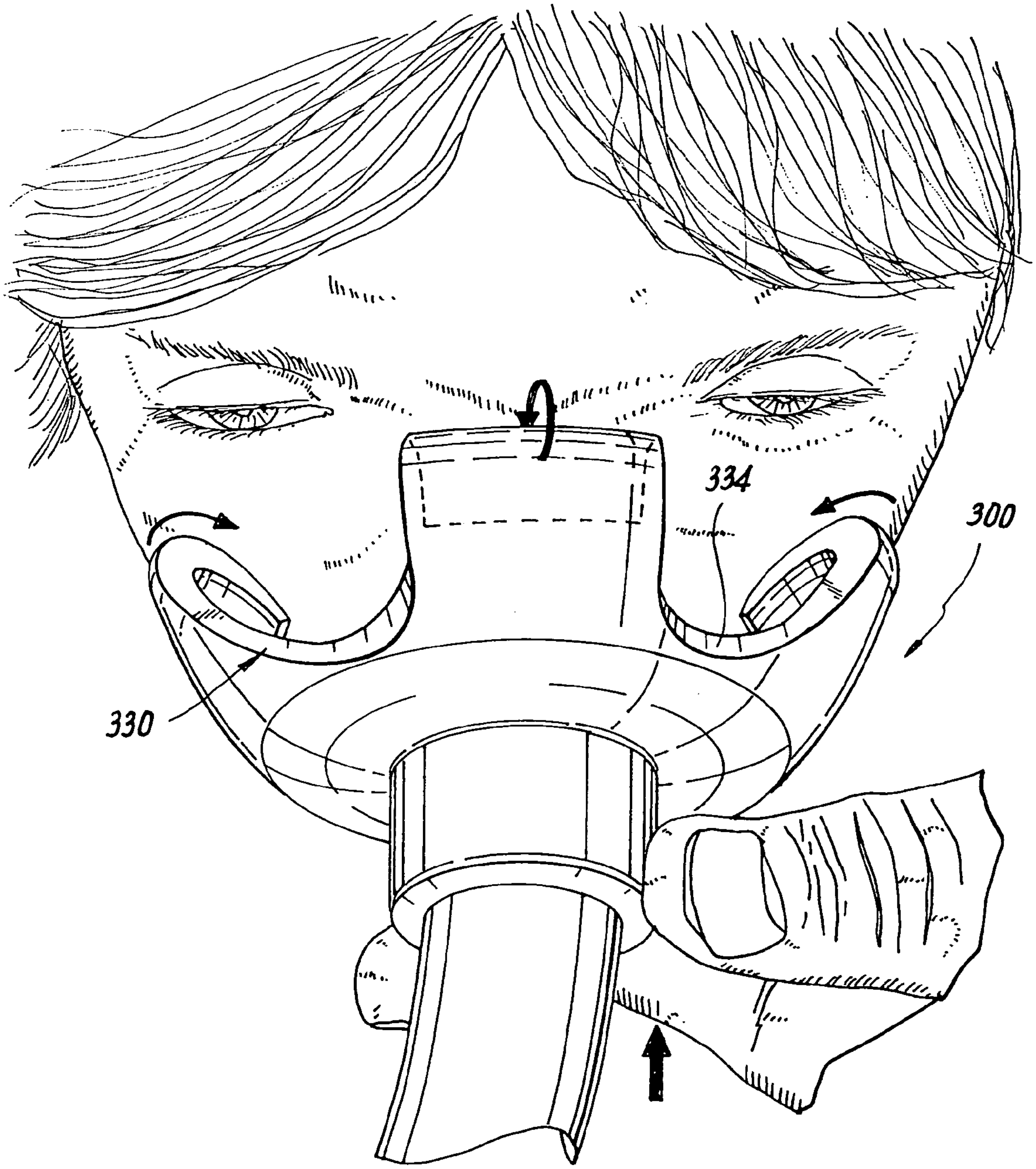
FIG. 8 is a perspective view of the face mask of FIG. 6 being placed in the typical administering position on the patient with the partially folded body being compressed and folded resulting in a reduction in size of the eye vents.

FIGS. 6–8 illustrate another embodiment where the eye vents 330 are more pronounced both in a state where the mask 300 is relaxed before the face mask 300 is applied to the face and after the face mask 300 is compressed as a result of a force being applied to the face. In other words, the eye vents 330 in FIGS. 6–8 are larger than the eye vents 330 formed in FIGS. 3–5. As with the other embodiments, the eye vents 330 in FIGS. 6 and 7 can be formed to have any number of different shapes. The embodiment of FIGS. 6–8 is used to illustrate that the eye vents can be formed in different sizes which directly results in a difference in the size of the vent opening when the face mask is applied against the user's face. It will therefore be appreciated that the face mask with the larger eye vent 330 in terms of surface area in the relaxed state will have the larger eye vents in the normal operating or applied state when the face mask is in contact with and seats against the face of the patient. In either embodiment, there is at least a small slit or the like formed between the inner edge 324 and the face to permit the drug to be vented as previously described.

As used herein, the term "bottommost edge or surface" describes an edge or surface of the face mask that is in contact with and seated against the face of the patient during normal application of the face mask to the face of the patient. As such, at least a portion of the bottommost edge or surface will contact and seat against the facial tissue (cheeks) of the patient.

Figure 9:
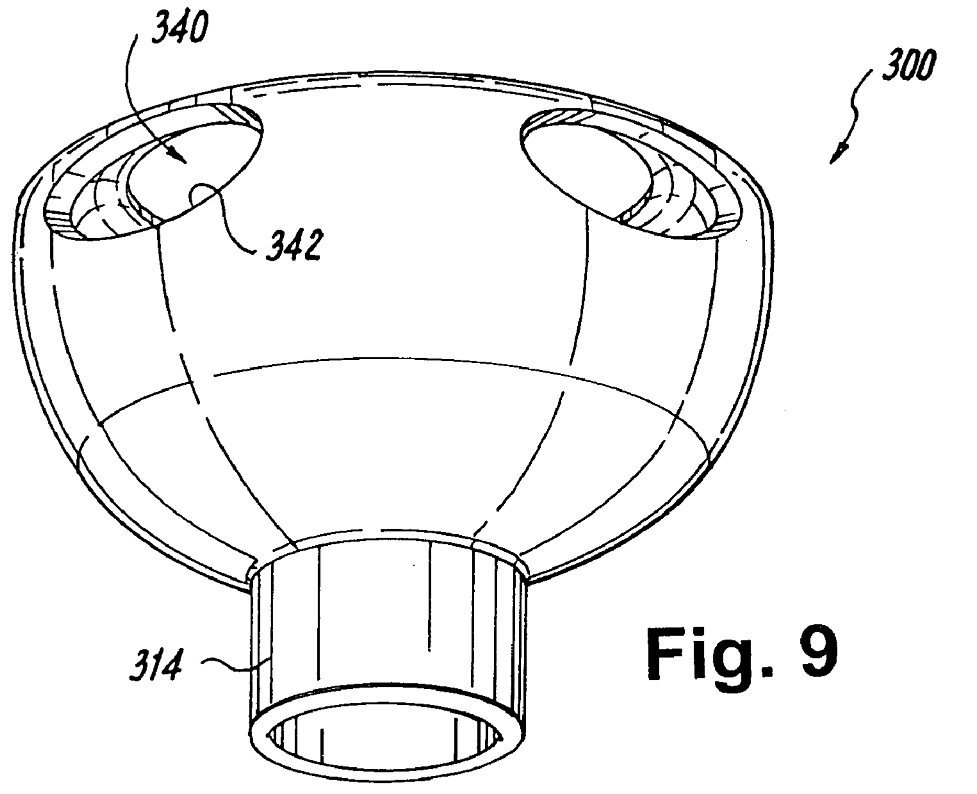
FIG. 9 is a top perspective view of a face mask according to a third exemplary embodiment for use as part of a nebulizer drug delivery system and prior to being placed in a typical administering position on a patient.
Figure 10:
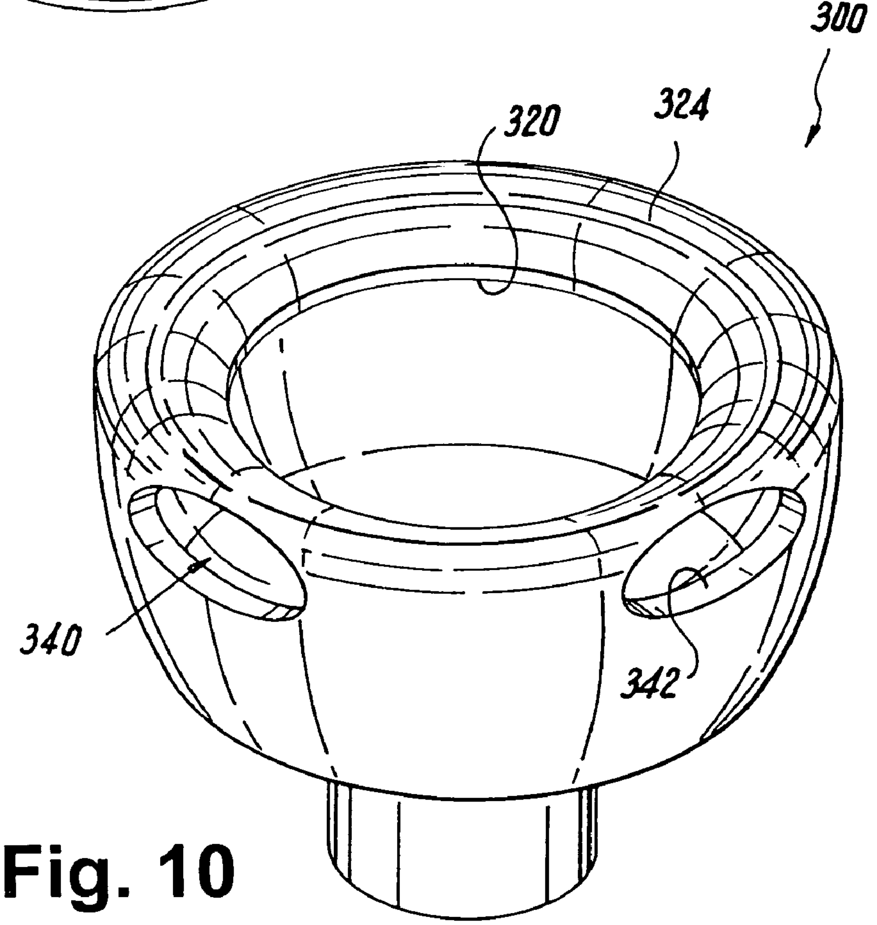
FIG. 10 is a bottom perspective view of the face mask of FIG. 9.
Figure 11:
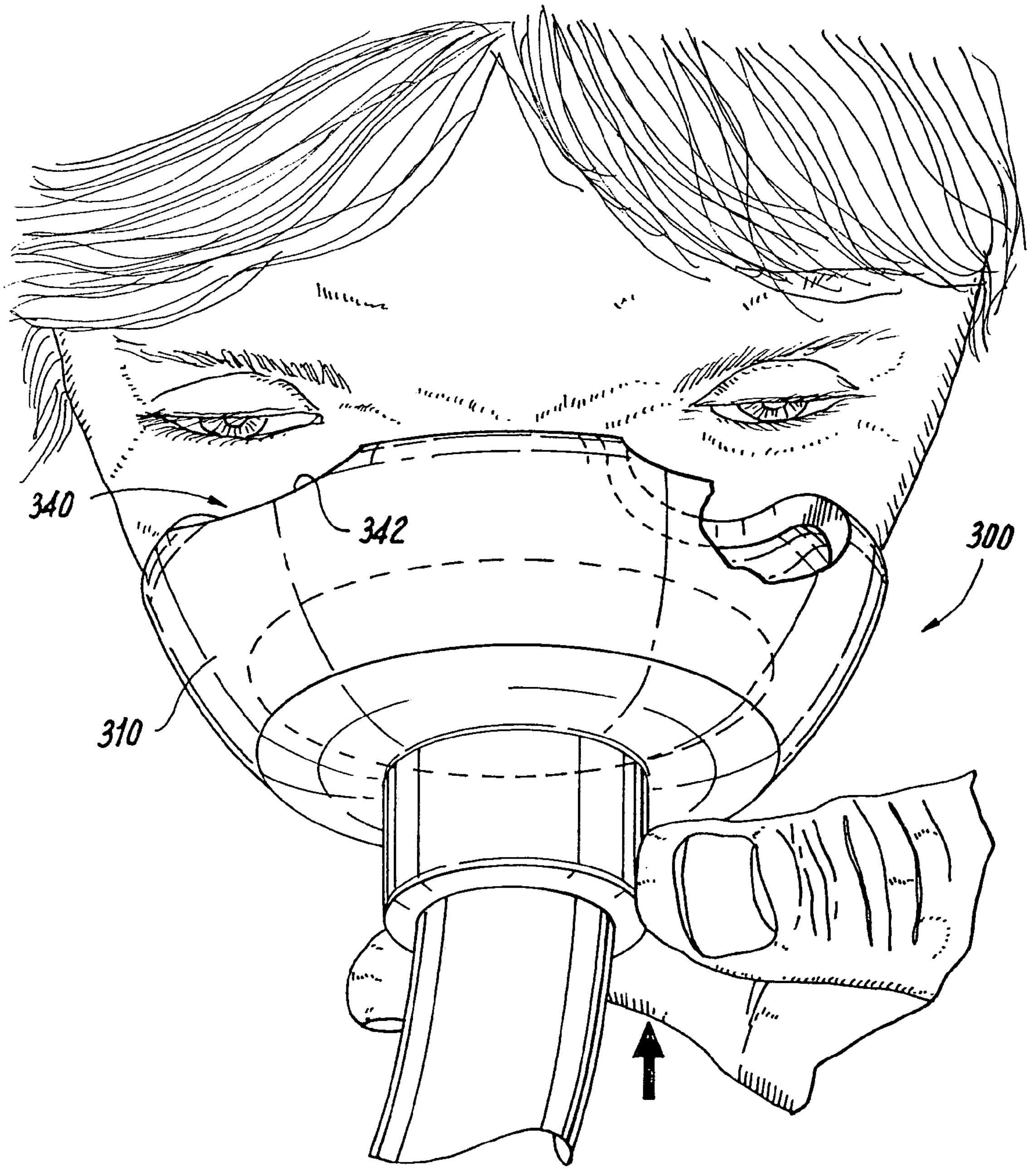
FIG. 11 is a perspective view of the face mask of FIG. 9 being placed in the typical administering position on the patient with the partially folded body being compressed and folded resulting in a reduction in size of the eye vents.

Now referring to FIGS. 9–11, in yet another embodiment, eye vents 340 are formed in the partially deformable face mask 300 such that each eye vent 340 is a completely bounded opening. In other words, the eye vent is defined by and has the mask body completely surrounding the eye vent ("completely bounded"). However, when the face mask 300 is placed against the user's face, the bottommost portion of the face mask compresses (collapses) or further folds over such that the eye opening is positioned relative to the face such that an opening is formed between an inner edge 342 of the eye and the face underneath the eyes of the patient. In this embodiment, the eye vents 340 are not open to and in communication with the second central opening 320 which is formed in the mask body and is for placement over the mouth of the patient.

The eye vents 340 can have any number of different shapes, such as circular, oval, square, rectangular, oblong, etc., and sizes so long as each is a completely bounded opening that is positioned in the bottommost portion such that when the face mask is placed and held against the face resulting in the face mask collapsing, the eye vent is positioned against the face such that an opening is formed between the inner edge 342 and the face to permit passage and venting of the drug. While the eye vent 340 may be formed so that it initially is not part of the bottommost portion of the face mask, the deformability of the face mask body causes the body to collapse (further fold), thereby drawing the eye vents 340 closer towards the face. In any event and as with the other embodiments, the eye vents 340 that are located underneath the eyes directly interact with the patient's face to provide openings at least between the inner edge 342 and the face itself to permit passage and outflow of the aerosolized drug that is present within the interior cavity. In other words, the collapsing or further folding action of the mask body causes the eye vents 340 to move into position against the face of the user. It will be understood that the eye vents 340 do not have to be in direct contact with the face of the patient but rather, the eye vents 340 can be located proximate the face with material of the mask body that is between the eye vent 340 and the second opening 320 being a surface that lies against the face of the patient. However even in this configuration, the eye vents 340 are directly underneath the eyes and serve to effectively vent the aerosolized drug as disclosed herein.

It will also be appreciated that the eye vents 340 can be formed in a more rigid type mask, identical to or similar to the one disclosed in the previously disclosed patent application. In other words, the eye vents 340 are spaced from the peripheral edge of the rigid mask which contacts and seats against the face of the patient during administration of the drug. In this embodiment, the mask does not "roll" over on itself and therefore, the eye vents 340 remain very well defined throughout the application, while they are still spaced from the peripheral edge. However, the eye vents should be formed in close proximity to the peripheral edge since the venting action should cause the vented drug to pass directly in front of but not in contact with the eyes of the patient, as generally shown in FIG. 5.

As the data contained in Table 1 below reflects, using a conventional Laerdal mask (pediatric silicone mask for resuscitation) with a nebulizer resulted in 1.00% of the aerosolized drug (in this case $Tc^{99}m$ labeled saline) initially placed in the nebulizer being deposited in the region of the eyes of the patient (1.54% of the aerosolized drug was deposited on the face). The inhaled mass for the face mask was 6.09% of the amount placed in the nebulizer.

When the face mask 300 of FIG. 3 was used, the inhaled mass increased to 8.05%, while at the same time, the amount of aerosolized drug being deposited in the region of the eyes was 0.12% as compared to 1.00% being deposited in the region of the eyes in the conventional, standard face mask, as shown in the Table 1. Thus, the use of the face mask 300 results in a substantial decrease in the amount of aerosolized drug that was deposited in the region of the eyes as compared to a standard, conventional face mask. However, this data merely quantifies the results and does not characterize the flow properties of the aerosolized drug that does escape underneath the face mask and flows toward the eyes. In other words and as previously mentioned, the safety benefits accorded by the face mask are improved if not only less aerosolized drug is deposited in the region of the eyes, as well as on the face for that matter, but also the flow characteristics of the escaping aerosolized drug are modified in the region of the eyes. The provision of eye vents in the face mask accomplishes these goals and enhances the overall safety of the face mask.

When the face mask 300 of FIG. 6 was used, the inhaled mass increased to 6.92%, while at the same time, the amount of aerosolized drug being deposited in the region of the eyes decreased substantially to 0.10% as compared to 1.00% being deposited in the region of the eyes in the conventional face mask, as shown in the Table 1. Thus, the use of the face mask 300 results in a substantial decrease in the amount of aerosolized drug that was deposited in the region of the eyes as compared to a standard, conventional face mask. More specifically, the modification of the face mask by forming eye vents reduced eye deposition substantially, while at the same time, there was an increase in the percent of aerosolized drug that was inhaled. The full advantages of the eye vents have been described previously herein.

Figure 12:
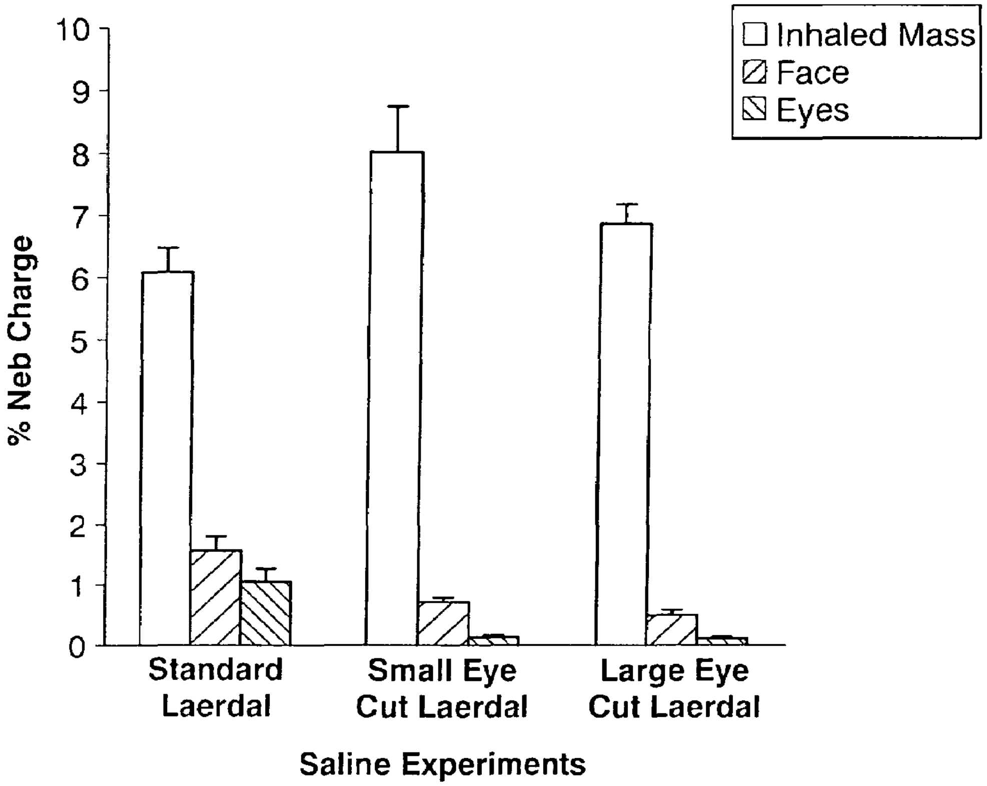
FIG. 12 is a schematic diagram in the form of a bar graph comparing drug delivery and facial deposition data obtained from testing a set of the exemplary face masks disclosed herein, with labeled saline serving as the aerosolize drug.
Figure 13:
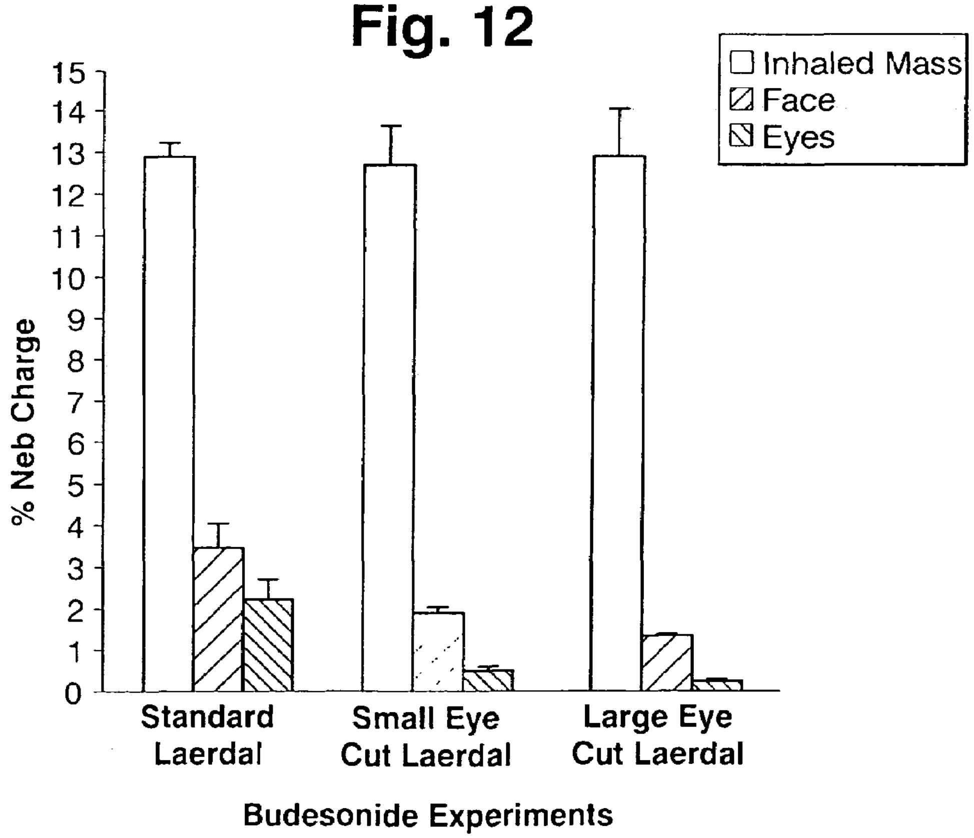
FIG. 13 is a schematic diagram in the form of a bar graph comparing drug delivery and facial deposition data obtained from testing a set of the exemplary face masks disclosed herein, with budesonide serving as the aerosolized drug.

FIG. 12 is a bar graph that represent a first set of the data set forth in Table 1.

A second experiment was conducted in which the steroid Budesonide was used as the aerosolized drug and the three above described masks were used in a nebulizing system. As the data contained in Table 1 below reflects, using a conventional Laerdal mask with a nebulizer resulted in 2.20% of the aerosolized drug (Budesonide) initially placed in the nebulizer being deposited in the region of the eyes of the patient (3.48% of the aerosolized drug was deposited on the face). The inhaled mass for the face mask was 12.90% of the amount placed in the nebulizer.

When the face mask 300 of FIG. 3 was used, the inhaled mass did not change significantly and had a value of 12.68%, while at the same time, the amount of aerosolized drug being deposited in the region of the eyes decreased substantially to 0.48% (1.86% deposited on the face) as compared to 2.20% being deposited in the region of the eyes in the conventional face mask, as shown in the Table 1. Thus, the use of the face mask 300 results in a substantial decrease in the amount of aerosolized drug that was deposited in the region of the eyes as compared to a standard, conventional face mask. However, this data merely quantifies the results and does not characterize the flow properties of the aerosolized drug that does escape underneath the face mask and flows toward the eyes. In other words and as previously mentioned, the safety benefits accorded by the face mask are improved if not only less aerosolized drug is deposited in the region of the eyes, as well as on the face for that matter, but also the flow characteristics of the escaping aerosolized drug are modified in the region of the eyes. The provision of eye vents in the face mask accomplishes these goals and enhances the overall safety of the face mask.

When the face mask 300 of FIG. 6 was used, the inhaled mass did not change significantly and had a value of 12.84%, while at the same time, the amount of aerosolized drug being deposited in the region of the eyes decreased substantially to 0.21% (1.30% deposited on the face) as compared to 2.20% being deposited in the region of the eyes in the conventional face mask, as shown in the Table 1. Thus, the use of the face mask 300 results in a substantial decrease in the amount of aerosolized drug that was deposited in the region of the eyes as compared to a standard, conventional face mask. More specifically, the modification of the face mask by forming eye vents reduced eye deposition substantially, while at the same time, there was an increase in the percent of aerosolized drug that was inhaled. The full advantages of the eye vents have been described previously herein.

FIG. 12 is a bar graph that represent some of the data set forth in Table 1.

TABLE 1

LAERDAL MASK AND MODIFICATIONS: COMBINED EXPERIMENTS

| Experiment Description | Laerdal "Type" Mask | Number of Experiments N | Mean Deposition as % neb charge Inhaled Mass | Face | Eyes |
|---|---|---|---|---|---|
| (Combined) $Tc^{99}m$ LABELLED SALINE | Standard | 8 | 5.93 | 1.95 | 1.39 |
| | | | 8.02 | 1.34 | 0.92 |
| | | | 6.54 | 1.24 | 0.75 |
| | | | 5.18 | 0.50 | 0.11 |
| | | | 4.90 | 2.94 | 2.31 |
| | | | 7.09 | 1.11 | 0.51 |
| | | | 6.46 | 1.55 | 0.77 |
| | | | 4.60 | 1.72 | 1.25 |
| | | MEAN | 6.09 | 1.54 | 1.00 |
| | | SD | 1.17 | 0.71 | 0.66 |
| | | SE | 0.41 | 0.25 | 0.23 |
| | Small Eye Cut | 7 | 9.57 | 0.97 | 0.15 |
| | | | 8.53 | 0.65 | 0.16 |
| | | | 6.82 | 0.54 | 0.17 |
| | | | 6.98 | 0.62 | 0.07 |
| | | | 6.10 | 0.44 | 0.05 |
| | | | 11.63 | 1.00 | 0.20 |
| | | | 6.75 | 0.70 | 0.07 |
| | | MEAN | 8.05 | 0.70 | 0.12 |
| | | SD | 1.98 | 0.21 | 0.06 |
| | | SE | 0.75 | 0.08 | 0.02 |
| | Large Eye Cut | 2 | 6.57 | 0.40 | 0.09 |
| | | | 7.26 | 0.55 | 0.11 |
| | | MEAN | 6.92 | 0.48 | 0.10 |
| | | SD | 0.49 | 0.11 | 0.01 |
| | | SE | 0.34 | 0.07 | 0.01 |
| (Combined) BUDESONIDE | Standard | 3 | 13.66 | 2.63 | 1.31 |
| | | | 12.32 | 3.29 | 2.32 |
| | | | 12.73 | 4.52 | 2.97 |
| | | MEAN | 12.90 | 3.48 | 2.20 |
| | | SD | 0.69 | 0.96 | 0.84 |
| | | SE | 0.40 | 0.55 | 0.48 |
| | Small Eye Cut | 3 | 14.38 | 1.79 | 0.39 |
| | | | 12.71 | 2.13 | 0.63 |
| | | | 10.95 | 1.67 | 0.42 |
| | | MEAN | 12.68 | 1.86 | 0.48 |
| | | SD | 1.72 | 0.24 | 0.13 |
| | | SE | 0.99 | 0.14 | 0.08 |
| | Large Eye Cut | 3 | 15.27 | 1.21 | 0.20 |
| | | | 11.60 | 1.28 | 0.20 |
| | | | 11.64 | 1.42 | 0.23 |
| | | MEAN | 12.84 | 1.30 | 0.21 |
| | | SD | 2.11 | 0.11 | 0.02 |
| | | SE | 1.22 | 0.06 | 0.01 |

The following examples are merely for purpose of illustration only and are not limiting of the present invention in any way.

EXAMPLE 1

A face mask as shown in FIGS. 3–5 according to the first embodiment was constructed and has the following dimensions. An outer diameter of the mask body 310 is about 77 mm and an outer diameter of the flange 314 being about 20 mm. The second opening 320 has a diameter of about 46 mm. As will be appreciated by viewing the figures, the eye vents 330 have a tapered construction in that a width thereof is greatest at the inner edge 334 and is less where the eye vent 330 communicates with the second opening 320. According to one embodiment, the width of the eye vent 330 at the inner edge 334 is about 20 mm and then it tapers to a diameter of about 10 mm where the vent opening 330 communicates with the second opening 320. The depth of the eye vent 330 as measured from the inner edge 334 to the bottommost portion 324 is about 9 mm in the relaxed state shown in FIGS. 3–4 and when applied to the face during administration of the drug, the depth decreases to about 5 mm.

EXAMPLE 2

A face mask as shown in FIGS. 6–8 according to the first embodiment was constructed and has the following dimensions. The face mask has the same dimensions as set forth in Example 1 above with the following exceptions. The depth of the eye vent 330 as measured from the inner edge 334 to the bottommost portion 324 is about 27 mm in the relaxed state shown in FIGS. 3–4 and when applied to the face during administration of the drug, the depth decreases to about 17 mm.

It will be appreciated that during application, the depth of the eye vent 330 or eye vents 340 in the embodiment in FIGS. 9–11 decreases any where from about 30% to 70% relative to its original depth, and according to one embodiment. In another embodiment, the depth decreases from about 40% to about 60% of its original depth, e.g., about 50%.

The present applicant has determined that the major determinant of facial deposition during inhalation of aerosolized drug using a pressurized wet nebulizer system is the effect of facemask design on the ballistic properties of the aerosol particles as they approach the surface of the face. There are two areas of facial deposition that illustrate these principles, namely (1) the velocity of gas carrying aerosol particles through leaks at the interface of the mask and the face is important and (2) patterns of deposition over the entire face including the forehead, the cheeks and other facial areas are influenced by the overall velocity of particles as they enter the mask from connections leading from the nebulizer itself.

With respect to the first area, the data and discussion hereinbefore demonstrates the importance of the velocity of the gas carrying aerosol particles, especially in the areas of the nasal labial folds and the eyes. High velocities in this region direct particles into the eyes resulting in deposition. This pattern of deposition is greatly mitigated by the localized eye vents or "eye cuts" formed in the mask which reduce the linear velocity of aerosol particles preventing deposition.

Figure 14A:
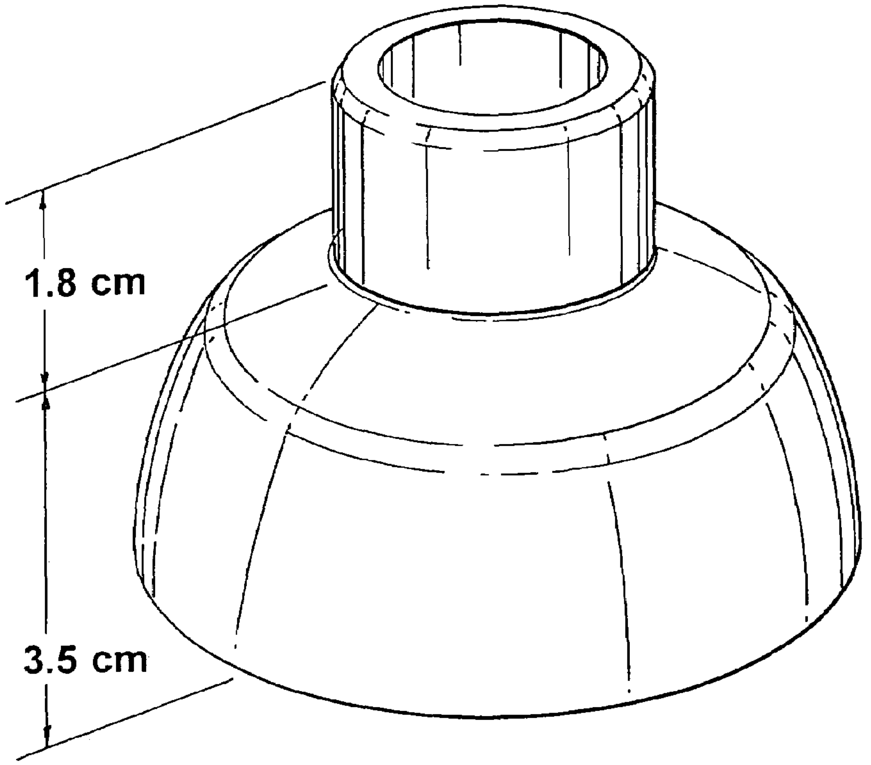
Figure 14B:
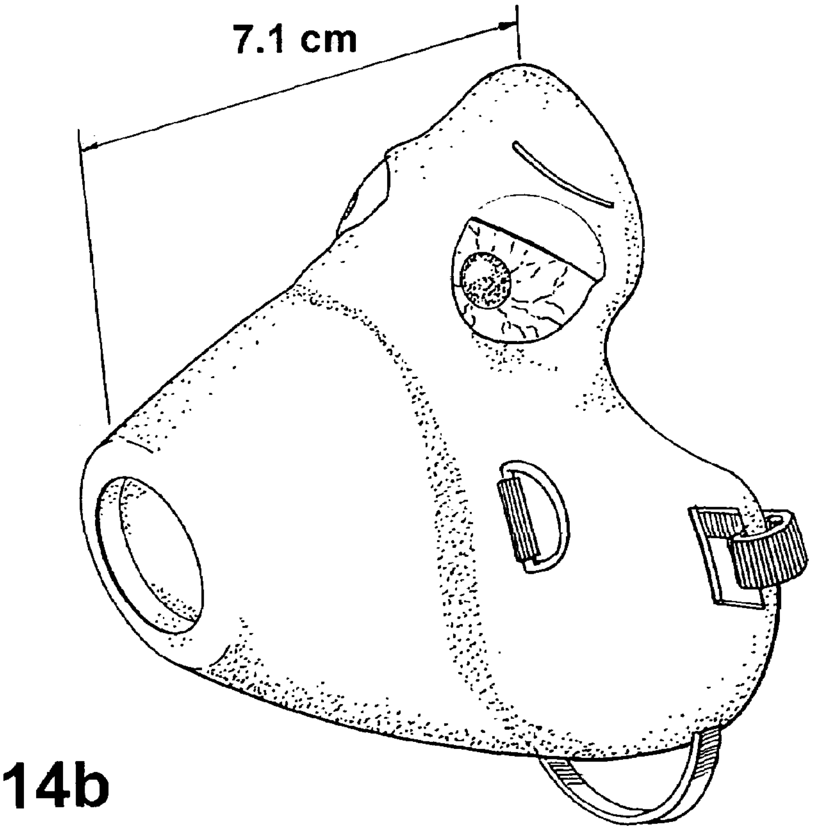

With respect to the second area, deposition patterns over the entire facer are influenced by the overall velocity of particles as they enter the mask from the nebulizer connection and this pattern is best illustrated utilizing nebulizers and conventional masks that are inserted perpendicular to the axis of the mouth, such as a facemask system that is commonly referred to as the "Salter" facemask system (See FIG. 14*d*). Under these conditions, particles are uniformly deposited over the face as well as in the eyes. Experiments have determined that this deposition is reduced significantly by increasing the distance of the insertion point of the nebulizer in the face mask from the face itself.

More specifically and as illustrated in FIG. 5, an exemplary face mask 300 includes the mask body 310 and the flange-like member 314 that extends outwardly from an outer surface 316 of the body 310 and in which the first central opening 312 is defined. The flange-like member 314 serves as a connector or interface between the nebulizer and the mask 300. The nebulizer typically has a stem or the like that is received within the flange-like member 314 so as to couple the two together. Accordingly, the point where the drug is discharged from the nebulizer is not the distal end of the flange-like member 314 but rather is closer to the end of the flange-like member 314 that joins and is integrally attached to the body 310.

Accordingly, the distance that is of interest begins with the location where the nebulizer stem terminates and extends to the face itself. This distance is shown as distance "A" in FIGS. 14A–D.

This increase in distance allows particles to proceed through the mask at reduced overall velocity because the particle stream leaving the nebulizer entering the mask has the opportunity to mingle with the flow regime within the mask which, because of increased linear cross section, results in reduced linear velocities as will be understood by viewing the constructions and data presented in the present Figs.

By optimizing and making changes in incremental distance from the facial surface ("the nozzle insertion distance"), facial deposition is significantly reduced for all of the various mask designs and is best illustrated in the component of facial deposition for the "panda" mask, which after the "eye cut" modification has the lowest deposition across the face separate from that of the eyes.

Figure 16A:
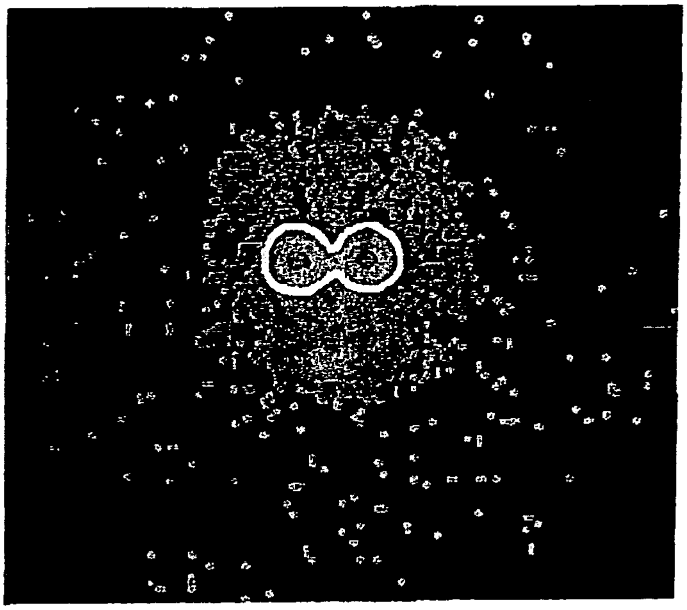
FIGS. 16A and B are images obtained using a gamma camera scan of a face model as part of a radiolabel face deposition study carried out using a conventional face mask and one showing a larger budesonide eye outline that is a larger area around the eyes for the purposes of illustrating particle deposition thereon.
Figure 16B:
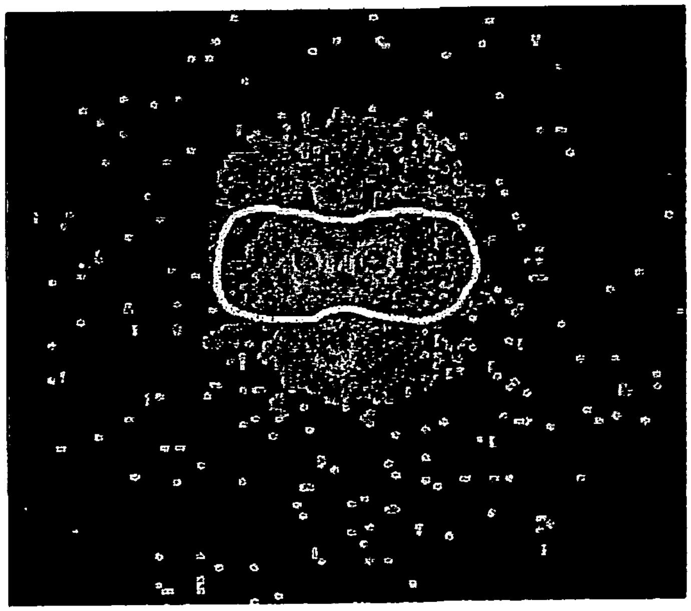
Figure 17:
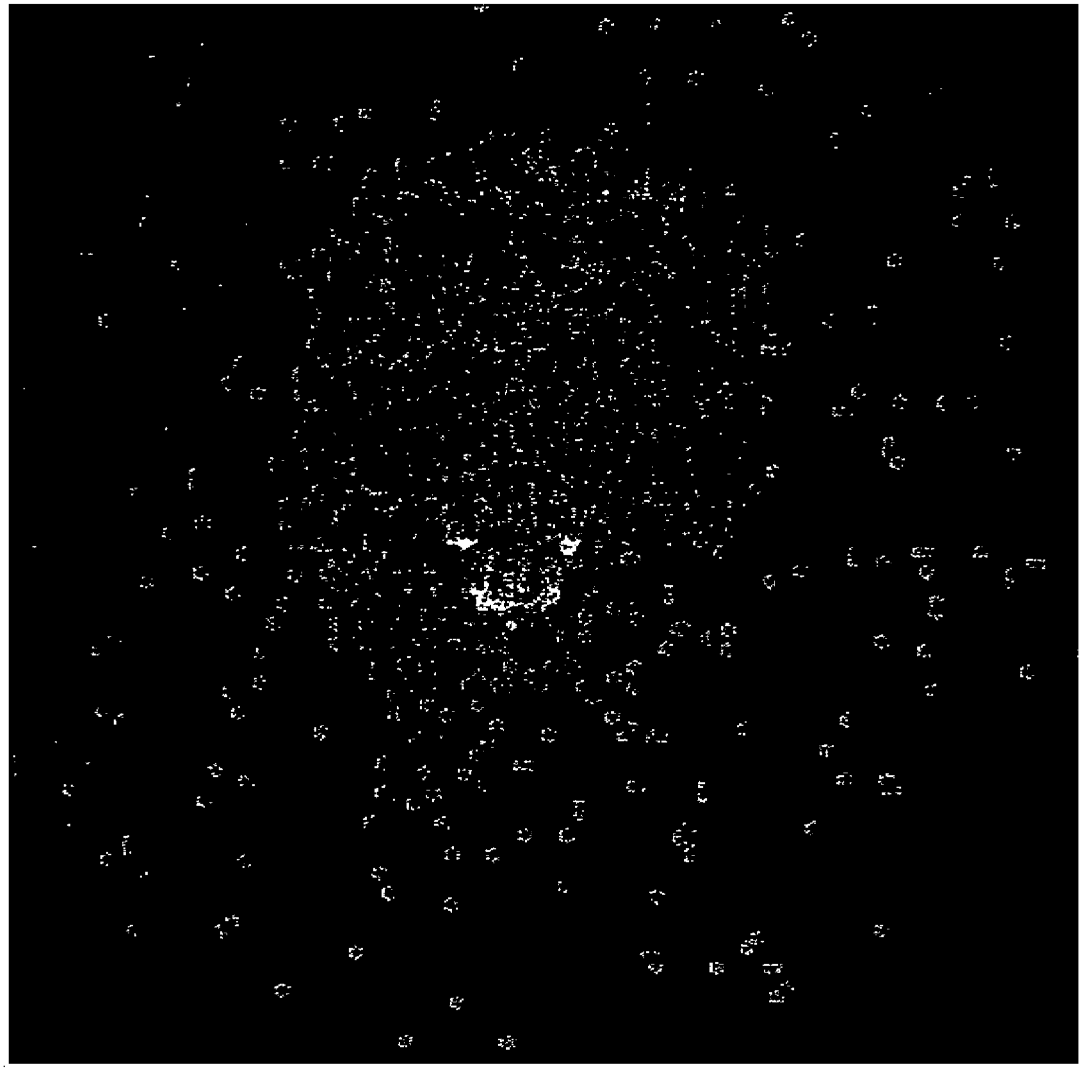
FIG. 17 is a gamma camera scan of a face model as part of a radiolabel face deposition study carried out using a Salter type face mask.

Review of the data in Table 2 in FIGS. 15A–B and the illustrative images of FIGS. 16A–B and 17 demonstrate that attention to the eye cuts as well as the nozzle insertion distance minimizes facial and eye deposition across all regions of the face (particularly the eyes from a maximum of 4.8% to 0.11–0.35%, and the remainder of the face of the face from a maximum of 1.74% to 0.98%). Inspection of Table 2 (FIGS. 15A–B) indicates that the eye deposition for the Laerdal mask is highest overall in its standard configuration Eye deposition is minimized with the presence of the eye cut modification. However, deposition over the rest of the face, while reduced significantly, is not as low as the panda mask with the eye cut modification. The major difference between the Laerdal and the panda configuration is the increased distance from the nozzle insertion point of the panda to the Laerdal which is approximately 1.7 cm. Thus, a mask design incorporating both principles (eye cut plus optimal nozzle length from face to nebulizer) will result in the greatest reduction in facial and eye deposition. Limitations on the nozzle insertion point distance from the face will be determined by construction constraints of masks as they are sized for faces of children and adults of different ages.

In one exemplary embodiment, the nozzle insertion distance, as measured from the insertion point of the nebulizer in the mask to the face, is optimized such that a reduction in the overall rate of facial deposition is on the order of at least 10%, preferably about 20% and more preferably greater than 20%, as compared to the same face mask containing just the eye cuts and a non-modified nozzle insertion distance. It will be understood that these values are merely exemplary in nature and that acceptable values can fall outside of these ranges. For example, a reduction of less than 10% may be realized and still be entirely effective and acceptable.

Accordingly, the process of optimizing the deposition rate on the face is at least a two part process according to one embodiment and more specifically, includes the formation of eye cuts in select predetermined locations as described hereinbefore and secondly, the nozzle insertion distance is selected so as to optimize the reduction in facial deposition. In other words, the velocity of the aerosolized drug being discharged into the face mask is modified and controlled by forming eye cuts in the face mask and then decreasing the velocity by increasing the distance from the insertion point of the nebulizer to the face.

In Table 2, under the heading "mask type", there are a number of different types of masks listed by a set of abbreviations. For example, the abbreviation "STD" refers to a standard off the shelf mask that does not include any modifications; the term "LEC" refers to large eye cuts being formed in the mask body; and the term "LEC-MOD" refers to a mask having large eye cuts as well as having a vent at the 6 o'clock position as mentioned hereinbefore. In addition, when the term "eye cut" is used under this heading, it refers to a mask that has standard eye cuts formed therein as opposed to the large size eye cuts that are denoted by the term "LEC".

It will further be appreciated that the nozzle insertion distance is selected so that even though a decrease in facial and eye deposition is realized, the amount of inhaled drug (e.g., measured as an inhaled mass percentage) remains within an acceptable range. For example and according to one embodiment, the nozzle insertion distance is greater than 5 cm and preferably is greater than 5.5 cm. In other embodiments, the nozzle insertion distance can be less than 5 cm or it can be greater than 5.5 cm so long as the effectiveness of the drug delivery is not jeopardized and the robustness of the mask likewise is not jeopardized as a result of increasing the length of the flange member 314.

Once again, the foregoing face mask designs and constructions apply not only to child face masks but also equally apply to young adult and adult face masks.

This aspect of the present invention can be seen by inspecting the data in Table 2 (FIGS. 15A–B) and more particularly, with reference to the budesonide experiments that can be used to see the results obtained with a face mask that contains the previously described eyecuts and has the snout optimized. In particular, comparison can be made between the "bubble eyecut" mask and the "original PP LEC" mask. For practical purposes, these masks are in essence the same mask and all the factors, such as the eyecuts, particle size, nebulizer, etc.) in the experiment are controlled except that the snout length is different. In particular, the snout length is increased from 5.0 to 7.1 (a 42% increase in size) that results in the face deposition value going from 2.40 to 1.33 (a 55% decrease in facial deposition). Similarly, another comparison and the same effect can be seen when comparing the Laerdal LEC (large eyecut) to the Pando LEC; again the face mask in essence is the same or very similar and the other factors, besides snout length, remain substantially the same. In this comparison, the snout was increased from 3.5 (Laerdal) to 5.2 (Panda), which is a 49% increase in the snout length, which results in the facial deposition dropping from 2.42 to 1.50 (a 62% decrease). Other comparison of in essence the same masks are the following: Laerdal stnd compared to the Panda stnd, both of these masks seal to the face (no vents) the only difference is the snout length and here the facial deposition is reduced from 2.42 to 1.72; another is the Laerdal standard to the Panda standard, where facial deposition was reduced from 6.51 to 1.72. Thus, according to one aspect of the present invention, the snout length of the mask is optimized by increasing the snout length at least 40% (compared to the original length), while at the same time, the facial deposition is decreased at least 50%, when compared to the unmodified face mask. It will be appreciated that this is merely one example of the present invention and other ranges can equally be used to accomplish the object of the present invention which is optimization of the snout length of the face mask so that facial deposition decreases.

The foregoing written description is of a preferred embodiment and particular features of the present invention and is not restrictive of the many applications or the breadth of the present invention which is instead defined by the claims appended hereto and substantial equivalents thereof.

What is claimed is:

1. A face mask for use in a pressurized drug delivery system, the face mask comprising:

an at least partially deformable body having a surface for placement against a face of a patient and a nose bridge section formed in an upper section of the body, the body having a pair of eye vents formed therein, with one eye vent being formed on one side of the nose bridge section and the other eye vent being formed on the other side of the nose bridge section, the eye vents for placement underneath the eyes of the patient when the face mask is placed against the face of the patient, wherein the eye vents are constructed so that when the body is placed against the face, an opening is formed between an innermost edge of the eye vent and the face underneath the eyes to permit venting, wherein the opening associated with the eye vent is open to atmospheric conditions and the face mask body includes a connector integral thereto, the connector defining a fluid pathway into an interior of the face mask and is constructed to receive, under pressure, an aerosolized drug.

2. The face mask according to claim 1, wherein the face mask is coupled to a nebulizer drug delivery system for delivering an aerosolized drug through the face mask.

3. The face mask according to claim 1, wherein each of the pair of vents comprises an eye cut out that is formed by removing material from the body.

4. The face mask according to claim 1, wherein the body includes a bottommost surface for contacting the face when the face mask is applied against the face and the body at least partially deforms.

5. The face mask according to claim 1, wherein the body has a bottom folded section where a portion of the body is folded over itself, the bottom folded section for placement against the face.

6. The face mask according to claim 5, wherein a central opening is formed in the bottom folded section and is for placement over a patient's mouth, the central opening being defined by a first body edge.

7. The face mask according to claim 6, wherein the eye vent extends from the inner edge to the central opening so that the central opening and eye vent are open to one another.

8. The face mask according to claim 6, wherein material of the body completely surrounds the eye vent which is spaced from the central opening.

9. The face mask according to claim 5, wherein the eye vent is at least partially formed in the bottom folded section.

10. The face mask according to claim 5, wherein the body is constructed such that the bottom folded section at least partially collapses when the face mask is applied against the face; however, the eye vent remains open so as to define the opening between the inner edge and the face to permit venting.

11. The face mask according to claim 5, wherein each eye vent is a completely bounded eye vent formed at least partially in the bottom folded section, the eye vent position in the bottom folded section such that when the face mask is applied against the face, the eye vent is proximate the face such that the opening is formed between the inner edge and the face.

12. The face mask according to claim 11, wherein the completely bounded vent opening has a shape selected from the group consisting of an oval, circle, square, and rectangle.

13. The face mask according to claim 1, wherein the eye vents abut and define the nose bridge section.

14. The face mask according to claim 1, wherein one end of each eye cut defines an outer section of the nose bridge section.

15. The face mask according to claim 1, wherein the distance between the distance from the distal end of the stem to the face is at least about 5 cm.

16. A face mask for use in a pressurized drug delivery system, the face mask comprising:

an at least partially deformable body having a surface for placement against a face of a patient and a nose bridge section formed in an upper section of the body, the body having a pair of eye vents formed therein, with one eye vent being formed on one side of the nose bridge section and the other eye vent being formed on the other side of the nose bridge section, the eye vents for placement underneath the eyes of the patient when the face mask is placed against the face of the patient, wherein the eye vents are constructed so that when the body is placed against the face, an opening is formed between an innermost edge of the eye vent and the face underneath the eyes to permit venting, wherein the eye vents occupy greater than 10% of a total surface area of the face mask body.

17. A face mask for use in a pressurized drug delivery system, the face mask comprising:

an at least partially deformable body having a forward section for coupling with equipment of the drug delivery system and a rear section for placement against a face of a patient, the rear section having a folded body configuration in that a wall defining the body is at least partially folded over itself and leads to a central opening for placement over a patient's mouth, the folded body being deformable when a force is applied against the forward section to place the body against the face, the rear section including a nose bridge section and a pair of eye vents formed on each side of the nose bridge section, the eye vents for placement underneath the eves of the patient when the face mask is placed against the face of the patient, wherein the eye vents are formed at least partially along the folded body and are constructed so that when the body is pressed against the face, an opening is formed between an innermost edge of the eye vent and the face underneath the eyes to permit venting, wherein the eye vent has a first depth, as measured from the inner edge thereof to a bottommost portion of the face mask, in a non-compressed state and a second depth in a compressed state when the mask is applied to face, the second depth being from about 30% to 70% less than the first depth.

18. The face mask according to claim 17, wherein the second depth is from about 40% to 60% less than the first depth.

19. A drug delivery system comprising:

a source of aerosolized drug; and a face mask including:

an at least partially deformable body having a surface for placement against a face of a patient and a nose bridge section formed in an upper section of the body, the body having a pair of eye vents formed therein, with one eye vent being formed on one side of the nose bridge section and the other eye vent being formed on the other side of the nose bridge section, the eye vents for placement underneath the eyes of the patient when the face mask is placed against the face of the patient and the face mask body folds over itself, wherein the face mask is operatively and fluidly connected to the source of aerosolized drug and vents the aerosolized drug to atmosphere through the eye vents.

20. The system according to claim 19, wherein the source of aerosolized drug includes a nebulizer drug delivery system for delivering the aerosolized drug through the face mask.

21. The system according to claim 19, wherein each of the pair of vents comprises an eye cut out that is formed by removing material from the body.

22. The system according to claim 19, wherein the body includes a bottommost surface for contacting the face when the face mask is applied against the face and the body at least partially deforms.

23. The system according to claim 19, wherein the body has a bottom folded section where a portion of the body is folded over itself, the bottom folded section for placement against the face.

24. The system according to claim 23, wherein a central opening is formed in the bottom folded section and is for placement over a patient's mouth, the central opening being defined by a first body edge.

25. The system according to claim 24, wherein the eye vent extends from the inner edge to the central opening so that the central opening and eye vent are open to one another.

26. The system according to claim 23, wherein the eye vent is at least partially formed in the bottom folded section.

27. The system according to claim 23, wherein the body is constructed such that the bottom folded section at least partially collapses when the face mask is applied against the face; however, the eye vent remains open so as to define the opening between the inner edge and the face to permit venting.

28. The system according to claim 23, wherein each eye vent is a completely bounded eye vent formed at least partially in the bottom folded section, the eye vent position in the bottom folded section such that when the face mask is applied against the face, the eye vent is proximate the face such that the opening is formed between the inner edge and the face.

29. The system according to claim 19, wherein the eye vents abut and define the nose bridge section.

30. The system according to claim 19, wherein one end of each eye cut defines an outer section of the nose bridge section.

31. A face mask for use in a pressurized drug delivery system, the face mask comprising:

an at least partially deformable body having a surface for placement against a face of a patient and a nose bridge section formed in an upper section of the body, the body having a pair of eye vents formed therein, with one eye vent being formed on one side of the nose bridge section and the other eye vent being formed on the other side of the nose bridge section, the eye vents for placement underneath the eyes of the patient when the face mask is placed against the face of the patient, the body including a flange member that extends outwardly from the mask body for receiving a stem associated with the drug delivery system to establish a connection between the pressurized drug delivery system and the mask, wherein a distance from a distal end of the stem to the face itself is optimized such that the optimization results in a decrease in facial deposition is greater than 40% compared to the face mask body with only eye vents formed therein.

32. The face mask according to claim 31, wherein the reduction in face deposition due to optimization of the distance is greater than 50%.

33. A face mask for use in a drug delivery system that delivers an aerosolized drug to a patient, the face mask comprising:

an at least partially deformable body having a surface contacting face for placement against a face of the patient and a nose bridge section formed in an upper section of the body, the body having a pair of eye vents formed therein on each side of the nose bridge section and being provided in perinasal sections of the mask that are prone to leakage of the aerosolized drug during administration of the aerosolized drug, wherein the features are constructed to reduce the particle inertia of any aerosolized drug that leaks through the perinasal sections and thereby reduce deposition of the aerosolized drug in eye regions of the patient by venting the aerosolized drug to atmosphere through the eye vents, wherein in an applied state when the mask is pressed against the face, the eye vents are placed against the face so as to form an opening between an inner edge of each eye vent and the face for venting the aerosolized drug, wherein the eye vents comprise completely bounded openings formed proximate and adjacent a peripheral edge of the face mask body such that when the face mask is applied, it folds over itself so as to define the opening, with a fold line of the face mask extending across and intersecting the opening.

* * * * *